US008870865B2

(12) United States Patent
Frankhouser et al.

(10) Patent No.: US 8,870,865 B2
(45) Date of Patent: Oct. 28, 2014

(54) MEDICAL TOOL FOR REDUCED PENETRATION FORCE WITH FEEDBACK MEANS

(71) Applicants: Paul L. Frankhouser, Bellefonte, PA (US); Maureen L. Mulvihill, Bellfonte, PA (US); Brian M. Park, Bellefonte, PA (US)

(72) Inventors: Paul L. Frankhouser, Bellefonte, PA (US); Maureen L. Mulvihill, Bellfonte, PA (US); Brian M. Park, Bellefonte, PA (US)

(73) Assignee: Actuated Medical, Inc., Bellefonte, PA (US)

( * ) Notice: Subject to any disclaimer, the term of this patent is extended or adjusted under 35 U.S.C. 154(b) by 0 days.

(21) Appl. No.: 13/672,497

(22) Filed: Nov. 8, 2012

(65) Prior Publication Data
US 2013/0072856 A1    Mar. 21, 2013

Related U.S. Application Data

(63) Continuation of application No. 12/559,383, filed on Sep. 14, 2009, now Pat. No. 8,328,738, which is a continuation-in-part of application No. 12/163,071, filed on Jun. 27, 2008, now Pat. No. 8,043,229.

(60) Provisional application No. 61/089,756, filed on Sep. 15, 2008, provisional application No. 60/937,749, filed on Jun. 29, 2007.

(51) Int. Cl.
*A61B 5/103* (2006.01)
*A61B 5/117* (2006.01)
(Continued)

(52) U.S. Cl.
CPC ............... *A61M 5/00* (2013.01); *A61B 10/025* (2013.01); *A61B 2017/00123* (2013.01); *A61B*
(Continued)

(58) Field of Classification Search
USPC .................. 600/573–584; 606/169, 181–185; 604/22
See application file for complete search history.

(56) References Cited

U.S. PATENT DOCUMENTS 4,623,335 A    11/1986 Jackson
4,771,660 A    9/1988 Yacowitz
(Continued)

FOREIGN PATENT DOCUMENTS

EP    0266058    5/1988
EP    1647255    4/2006
(Continued)

OTHER PUBLICATIONS

Meyer Jr., R.J., et al., "Displacement Amplification of Electroactive Materials Using the Cymbal Flextensional Transducer", Sensors and Actuators A 87 (2001) 157-162.
(Continued)

*Primary Examiner* — Sean Dougherty
(74) *Attorney, Agent, or Firm* — Neal P Pierotti; Metz Lewis Brodman Must O'Keefe

(57) ABSTRACT

A medical device for reducing the force necessary to penetrate living being tissue using a variety of reciprocating motion actuators, including piezoelectric, voice coil, solenoids, pneumatics or fluidics. The reciprocating actuator drives a penetrating member, such as a needle, through the tissue at a reduced force while the device detects the passage of the penetrating member through the tissue. Upon passage of the penetrating member through the tissue, electrical power to the reciprocating actuator is automatically terminated. One exemplary method for detecting this passage is via a fluid-containing syringe that is coupled to a channel within the penetrating member. Once the penetrating member tip has passed through the living tissue, the fluid within the syringe no longer experiences any pressure and a plunger within the syringe displaces indicating passage of the penetrating member tip. This motion can provide direct tactile feedback to an operator of the medical device or can automatically open a switch providing electrical power to the medical device. Alternatively, a pressure transducer can also monitor the pressure within the penetrating member channel and automatically activate the switch to cut off the electrical power.

20 Claims, 41 Drawing Sheets

(51) Int. Cl.
  *A61B 10/02* (2006.01)
  *A61M 5/00* (2006.01)
  *A61B 17/34* (2006.01)
  *A61M 5/20* (2006.01)
  *A61B 17/00* (2006.01)
  *A61B 19/00* (2006.01)
  *A61B 17/32* (2006.01)

(52) U.S. Cl.
  CPC ............... 17/3401 (2013.01); *A61B 2019/464* (2013.01); *A61B 17/3476* (2013.01); *A61B 2017/00115* (2013.01); *A61B 17/3415* (2013.01); *A61B 17/320068* (2013.01); *A61M 5/20* (2013.01)
  USPC ................ 606/42; 600/587; 606/181; 604/22

(56) References Cited

U.S. PATENT DOCUMENTS

| | | | |
|---|---|---|---|
| 4,911,161 A | 3/1990 | Schechter | |
| 5,024,662 A | 6/1991 | Menes et al. | |
| 5,403,276 A | 4/1995 | Schechter et al. | |
| 5,449,370 A | 9/1995 | Vaitekunas | |
| 5,471,102 A | 11/1995 | Becker et al. | |
| 5,575,789 A | 11/1996 | Bell et al. | |
| 5,647,851 A | 7/1997 | Pokras | |
| 5,681,283 A | 10/1997 | Brownfield | |
| 5,728,089 A | 3/1998 | Lal et al. | |
| 5,728,130 A | 3/1998 | Ishikawa et al. | |
| 5,729,077 A | 3/1998 | Newnham et al. | |
| 5,840,026 A | 11/1998 | Uber, III et al. | |
| 5,885,226 A | 3/1999 | Rubinstein et al. | |
| 6,019,775 A | 2/2000 | Sakurai | |
| 6,019,776 A | 2/2000 | Preissman et al. | |
| 6,068,604 A | 5/2000 | Krause et al. | |
| 6,096,004 A | 8/2000 | Meglan et al. | |
| 6,245,028 B1 | 6/2001 | Furst et al. | |
| 6,273,861 B1 | 8/2001 | Bates et al. | |
| 6,379,371 B1 | 4/2002 | Novak et al. | |
| 6,423,014 B1 | 7/2002 | Churchill et al. | |
| 6,443,910 B1 | 9/2002 | Krueger et al. | |
| 6,465,936 B1 | 10/2002 | Knowles et al. | |
| 6,491,708 B2 | 12/2002 | Madan et al. | |
| 6,497,714 B1 | 12/2002 | Ishikawa et al. | |
| 6,514,267 B2 | 2/2003 | Jewett | |
| 6,602,229 B2 | 8/2003 | Coss | |
| 6,673,086 B1 | 1/2004 | Hofmeier et al. | |
| 6,689,087 B2 | 2/2004 | Pal et al. | |
| 6,718,196 B1 | 4/2004 | Mah et al. | |
| 6,726,698 B2 | 4/2004 | Cimino | |
| 6,730,043 B2 | 5/2004 | Krueger et al. | |
| 6,785,572 B2 | 8/2004 | Yanof et al. | |
| 6,817,973 B2 | 11/2004 | Merril et al. | |
| 6,869,439 B2 | 3/2005 | White et al. | |
| 6,939,317 B2 | 9/2005 | Zacharias | |
| 6,942,677 B2 | 9/2005 | Nita et al. | |
| 6,984,220 B2 | 1/2006 | Wuchinich | |
| 7,018,343 B2 | 3/2006 | Plishka | |
| 7,025,774 B2 | 4/2006 | Freeman et al. | |
| 7,066,884 B2* | 6/2006 | Custer et al. | 600/309 |
| 7,206,626 B2 | 4/2007 | Quaid, III | |
| 7,244,266 B2* | 7/2007 | Garthe et al. | 606/181 |
| 7,252,648 B2* | 8/2007 | Honda et al. | 604/22 |
| 7,297,131 B2 | 11/2007 | Nita | |
| 7,335,997 B2 | 2/2008 | Wiener | |
| 7,364,567 B2 | 4/2008 | Beyerlein | |
| 7,374,544 B2 | 5/2008 | Freeman et al. | |
| 7,518,479 B2 | 4/2009 | Mask et al. | |
| 7,648,468 B2 | 1/2010 | Boecker et al. | |
| 7,651,475 B2 | 1/2010 | Angel et al. | |
| 7,651,490 B2 | 1/2010 | Boukhny et al. | |
| 7,654,825 B2 | 2/2010 | Ray | |
| 7,682,366 B2* | 3/2010 | Sakurai et al. | 606/128 |
| 7,776,027 B2 | 8/2010 | Manna et al. | |
| 2001/0014785 A1 | 8/2001 | Sussman et al. | |
| 2002/0026127 A1 | 2/2002 | Balbierz et al. | |
| 2002/0077589 A1 | 6/2002 | Tessari | |
| 2002/0183774 A1 | 12/2002 | Witt et al. | |
| 2002/0198555 A1 | 12/2002 | White et al. | |
| 2003/0078495 A1 | 4/2003 | Goodwin | |
| 2003/0109871 A1 | 6/2003 | Johnson et al. | |
| 2003/0195468 A1 | 10/2003 | Lal et al. | |
| 2003/0199899 A1 | 10/2003 | Boecker et al. | |
| 2004/0106894 A1 | 6/2004 | Hunter et al. | |
| 2004/0176717 A1* | 9/2004 | Honda et al. | 604/22 |
| 2004/0254599 A1* | 12/2004 | Lipoma et al. | 606/181 |
| 2004/0260240 A1 | 12/2004 | Beyerlein | |
| 2005/0033314 A1* | 2/2005 | Sakurai et al. | 606/127 |
| 2005/0148940 A1* | 7/2005 | Miller | 604/187 |
| 2006/0058783 A1 | 3/2006 | Buchman, III | |
| 2006/0122555 A1* | 6/2006 | Hochman | 604/67 |
| 2006/0142657 A1 | 6/2006 | Quaid et al. | |
| 2006/0149141 A1 | 7/2006 | Sheets | |
| 2007/0063618 A1 | 3/2007 | Bromfield | |
| 2007/0129628 A1 | 6/2007 | Hirsh | |
| 2007/0142766 A1 | 6/2007 | Sundar et al. | |
| 2007/0191758 A1 | 8/2007 | Hunter et al. | |
| 2007/0219496 A1 | 9/2007 | Kamen et al. | |
| 2007/0250113 A1 | 10/2007 | Hegeman et al. | |
| 2008/0021490 A1 | 1/2008 | Briggs et al. | |
| 2008/0103413 A1 | 5/2008 | Cicenas et al. | |
| 2008/0139961 A1 | 6/2008 | Slama et al. | |
| 2008/0147094 A1* | 6/2008 | Bittenson | 606/144 |
| 2008/0228104 A1 | 9/2008 | Uber et al. | |
| 2009/0069712 A1 | 3/2009 | Mulvihill et al. | |
| 2009/0247865 A1 | 10/2009 | Spohn et al. | |
| 2010/0010505 A1 | 1/2010 | Herlihy et al. | |
| 2010/0036245 A1 | 2/2010 | Yu et al. | |
| 2012/0302956 A1* | 11/2012 | Bral | 604/112 |

FOREIGN PATENT DOCUMENTS

| | | |
|---|---|---|
| JP | 9239031 | 9/1997 |
| JP | 2001346874 | 12/2001 |
| WO | 2004091693 | 10/2004 |
| WO | 2008086560 | 7/2008 |
| WO | 2008097609 | 8/2008 |
| WO | 2009083600 | 7/2009 |
| WO | 2009092164 | 7/2009 |
| WO | 2009097621 | 8/2009 |

OTHER PUBLICATIONS

Podder, T.K., et al., "Effects of Velocity Modulation During Surgical Needle Insertion", Proceedings of the 2005 IEEE, Engineering in Medicine and Biology 27th Annual Conference, Sep. 1-4, 2005.
Luis, J., et al., "Rectangular Cymbal Arrays for Improved Ultrasonic Transdermal Insulin Delivery", J. Acoust. Soc. Am., vol. 122, Issue 4, Oct. 2007.
Yang, M., et al., "Microneedle Insertion Force Reduction Using Vibratory Actuation", Biomedical Microdevices 6:3, 177-182, 2004.
Piccin, et al., "A Robotized Needle Insertion Device for Percutaneous Procedures", Proceedings of IDETC/CIE 2005, 2006 ASME International Design Engineering Technical Conferences and Computers and Information in Engineering Conference, Long Beach, CA, USA, Sep. 24-28, 2005.
Loeffel, et al., "Development of an Advanced Injection Device for Highly Viscous Materials", European Cells and Materials, vol. 11, Supp. 1, 2006, p. 51.
Dario, et al., "Smart Surgical Tools and Augmenting Devices", IEEE Transactions on Robotics and Automation, vol. 19, No. 5, Oct. 2003, pp. 782-792.
"Sonic Drill Could Go Into Space", R&D, Sep. 2000, p. 135.
Goethals, P., "Tactile Feedback for Robot Assisted Minimally Invasive Surgery: An Overview", Division PMA, Department of Engineering, K.U. Leuven, Jul. 14, 2008.
Zorcolo, et al., "Catheter Insertion Simulation with Combined Visual and Haptic Feedback", Center for Advanced Studies, Research and Development in Sardinia, 09101 Uta (CA) Italy; Proceedings of the First PHANToM Users Research Symposium, May 21-22, 1999, Deutsches Krebsforschungszentrum, Heidelberg, Germany.

(56) References Cited

OTHER PUBLICATIONS

Kwon, et al., "Realistic Force Reflection in the Spine Biopsy Simulator", IEEE International Conference on Robotics and Automation, 2001. Proceedings 2001 ICRA, May 21-26, 2001, Seoul, Korea 2001, vol. 2, 1358-1363.

"R&D 100 Awards Winners Reveal 21st Century Technologies", 38th Annual R&D Awards, R&D Research & Development, Sep. 2000, p. 135.

"Silicon-Based Ultrasonic Surgical Actuators", Amit Lal, Member, IEEE; Proceedings of the 20th Annual International Conference of the IEEE Engineering in Medicine and Biology Society, vol. 20, No. 6, 1998, pp. 2785-2790.

Terrett, et al., "3538 Study Assessing the Effectiveness of a Vibrating Dental Syringe Attachment", Pain Management, Oral Pathology, Malodor, and Indices, Mar. 13, 2004.

Lal, "Silicon-Based Ultrasonic Surgical Actuators", Proceedings of the 20th Annual Conference of the IEEE in Medicine and Biology Society, vol. 20, No. 6, 1998, pp. 2785-2790.

Hing, et al., Reality-Based Needle Insertion Simulation for Haptic Feedback in Prostate Brachytherapy, Proceedings of the 2006 IEEE International Conference on Robotics and Automation, Orlando, Florida, May 2006.

International Preliminary Report on Patentability for PCT Application No. PCT/AU2008/000019, dated Jul. 21, 2009.

International Search Report for PCT Application No. PCT/US2009/060387, dated May 18, 2010.

International Search Report for PCT Application No. PCT/US2009/056864, dated Apr. 26, 2010.

Zorcolo, et al., "Catheter Insertion Simulation With Combined Visual and Haptic Feedback", Center for Advanced Studies, Research and Development in Sardinia 09101 Uta (CA) Italy; Proceedings of the First PHANTOM Users Research Symposium, May 21-22, 1999, Deutsches Krebsfordschungszentrum, Heidelberg, Germany, Date of public disclosure is May 21, 1999.

"Mark V ProVis Angiographic Injection System", Medrad, Inc., Copyright 2006-2010; http://www.medrad.com/en-us/info/products/Pages/MarkVProVisInjector.aspx; Copyright 2010; Accessible via www.archive.org and showing page capture on Feb. 7, 2010 and Mar. 30, 2010; date of public disclosure is Feb. 7, 2010.

Hing, et al., "Reality-Based Estimation of Needle and Soft-Tissue Interaction for Accurate Haptic Feedback in Prostate Brachytherapy Simulation", Program for Robotics, Intelligent Sensing, and Mechatronics (PRISM) Labaoratory, Drexel University, Philadelphia, PA, Drexel University College of Medicine, Philadelphia, PA; in International Symposium of Robotics Research, San Francisco, California, Oct. 12-15, 2005; date of public disclosure is Oct. 12, 2005.

* cited by examiner

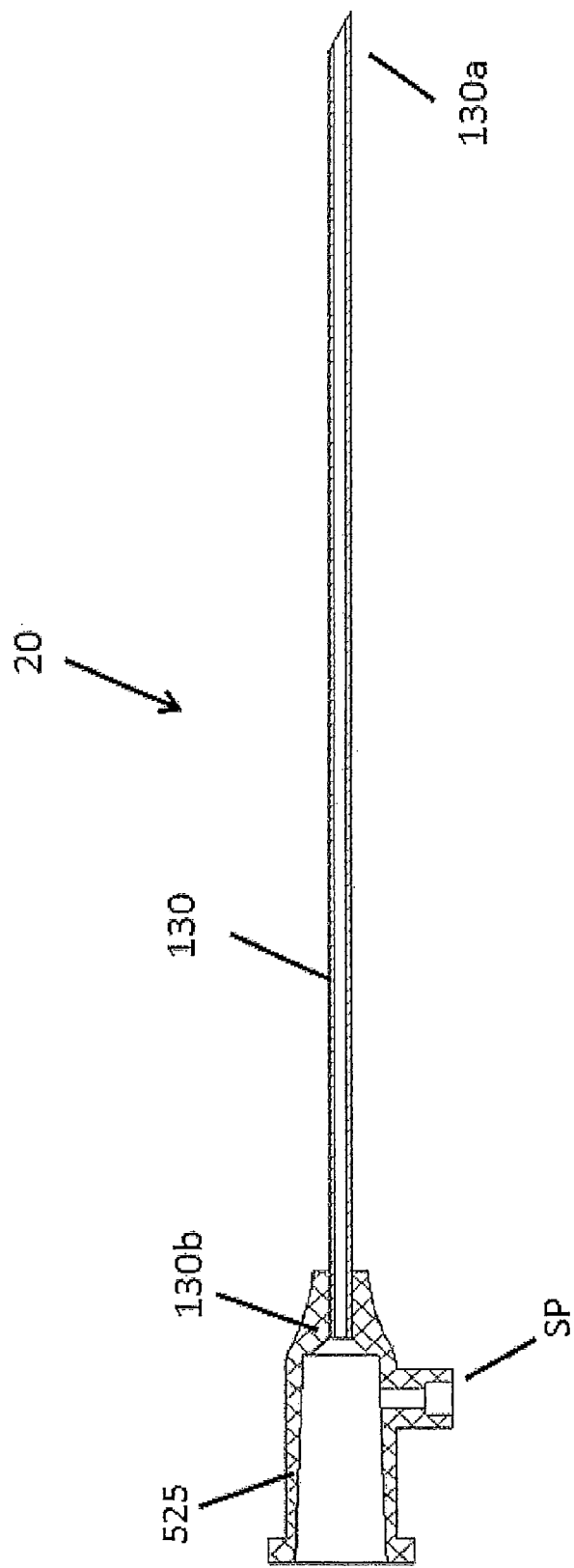

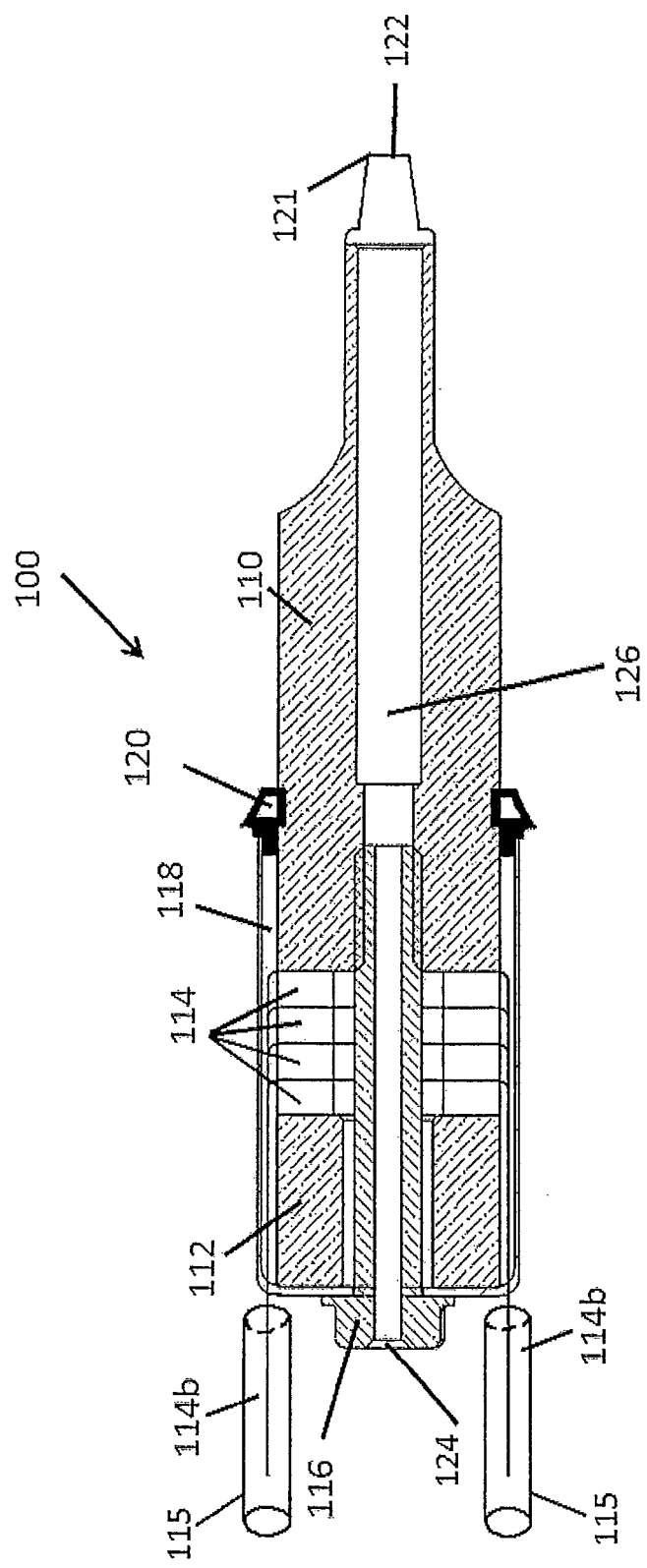

MEDICAL TOOL FOR REDUCED PENETRATION FORCE WITH FEEDBACK MEANS

This divisional application claims the benefit under 35 U.S.C. §120 of U.S. application Ser. No. 12/559,383, filed on Sep. 14, 2009, entitled MEDICAL TOOL FOR REDUCED PENETRATION FORCE WITH FEEDBACK MEANS, which claims the benefit under 35 U.S.C. §119(e) of U.S. Provisional Application Ser. No. 61/089,756, filed Sep. 15, 2008, entitled MEDICAL TOOL FOR REDUCED PENETRATION FORCE WITH FEEDBACK MEANS, and is also a continuation-in-part of U.S. application Ser. No. 12/163,071, filed on Jun. 27, 2008, entitled MEDICAL TOOL FOR REDUCED PENETRATION FORCE, which issued as U.S. Pat. No. 8,043,229 on Oct. 25, 2011, which in turn claims the benefit under 35 U.S.C. §119(e) of U.S. Provisional Application No. 60/937,749, filed Jun. 29, 2007, entitled RESONANCE-DRIVEN VASCULAR ENTRY NEEDLE, and all of whose entire disclosures are incorporated by reference herein.

STATEMENT REGARDING FEDERALLY SPONSORED RESEARCH OR DEVELOPMENT

This invention was made with government support under contract numbers 1R43GM085844-01, 1R43RR02493-01A2, and 1R43CA139774-01A1 awarded by the National Institutes of Health. The government has certain rights in the invention.

BACKGROUND OF THE INVENTION

1. Field of the Invention

The present invention generally pertains to handheld medical devices, and more specifically to electrically driven lancets; epidural catheter inserters; biopsy medical instruments, such as bone biopsy medical devices; vascular entry penetrating members, spinal access needles and other catheterization needles. The invention is applicable to the delivery and removal of blood, tissues, medicine, bone marrow, nutrients or other materials within the body.

2. Description of Related Art

Epidural anesthesia is a form of regional anesthesia involving injection of drugs directly into the epidural space. To begin the procedure, a needle is inserted from the outer layer of skin, through several layers of tissue and finally placed within the epidural space, through which a catheter is optionally passed. Local anesthetics are injected into the epidural space causing temporary loss of sensation and pain by blocking the transmission of pain signals through nerves in or near the spinal cord. The procedure can be unpleasant to the patient because of the high force levels required for the relatively dull epidural needle to penetrate the supraspinous ligament, interspinous ligament and ligamentum flavum. One complication is that a clinician will accidently overshoot and puncture the dura because of this high force of penetration and an almost-instantaneous change in resistance upon passing the needle into the epidural space (i.e., high forward momentum followed by instantaneous minimization of force). Upon puncturing the dura, the cerebrospinal fluid can leak into the epidural space causing the patient to experience severe post dural puncture headache, lasting from days to possibly years. Significant leakage can cause enough intracranial hypotension as to tear veins, cause subdural hematoma, and traction injuries to the cranial nerves resulting in tinnitus, hearing loss, dizziness, facial droop, or double vision.

A bone marrow biopsy is used for diagnosing tumors and a variety of bone diseases. The most commonly used site for the bone biopsy is the anterior iliac crest. A major disadvantage is the force required to penetrate the bone tissue, and the twisting motion often used to force the needle inward, which results in patient discomfort as well as possible healing complications from damaged tissues. The penetration force can also be tiring for clinicians and lead to multiple sampling attempts. Complications are rare but can include bleeding, pain, and infection. Pain is minimized with proper local anesthesia, though the patient still experiences a pressure sensation during insertion and retraction during some procedures. Another problem is crushing the sample or being unable to retrieve part of all of it, limiting the ability to diagnose. As shown in FIG. 1, a biopsy tool PA1 typically comprises a handle (not shown) and hollow cannula 1 with cannula distal end 1' surrounding a stylet 2 attached to the handle. To penetrate through cortical bone, a clinician pushes the cannula and stylet through the bone to the marrow. The distal tip 3 of the inner stylet or trocar is sharpened and has an angled chisel-like face 4 which reduces the surface area to reduce the exertion force.

Currently, to minimize the possibility of a dura puncture, the epidural catheter insertion process is typically performed very slowly and with a 16-18 gauge, specially designed, relatively dull needle PA2, such as the one shown in FIG. 2 called a Tuohy needle 5. An epidural needle, such as the Tuohy needle 5 or Hustead needle, has a directional curved tip 6, which decreases the "sharpness" at the needle and, therefore, makes accidental dura puncture more difficult. The curved tip also facilitates directing an indwelling catheter into the epidural space and a tip opening 7 facilitates catheter or fluid introduction or removal. Unfortunately, this dull curved-tip design actually increases the force a clinician must use and makes it more difficult for a clinician to stop the forward momentum upon penetration of the dural space. Additionally, the Tuohy design increases the likelihood that a clinician relies on tactile feedback during penetration. In other words, during the insertion procedure a clinician will rely on feeling a "popping" sensation—indicative of passing the needle past the ligamentum flavum—to locate the tip of the needle within the epidural space and quickly stop the forward momentum being applied. Still, because penetration into other tissues, such as muscle, calcified ligament, or regular ligament may produce a similar popping, a clinician may not fully perceive the correct location of the needle tip where the tip of the needle is occluded until passing through these tissues.

Several alternate technologies have been developed that attempt to minimize the dura puncture risk, while also giving the clinician indication of successful epidural placement. For example, the detection method and apparatus disclosed in U.S. Patent Application Publication No. 2007/0142766 (Sundar, et al.), the contents of which are incorporated by reference, relies on a spring-loaded plunger pushing a fluid into the epidural space upon successful entry. Accordingly, the clinician is given a visual indicator (i.e., the movement of the plunger as the fluid experiences a loss of resistance at the needle opening), and would cease applying forward force. Similarly, U.S. Pat. No. 5,681,283 (Brownfield) also relies on a visual indicator to communicate successful entry of a needle into a cavity to the clinician. Unfortunately, while a visual indicator is a positive advancement, the actual cause of the accidental dural wall puncture—that is, the high force applied by the clinician against the needle to pass through the various tissue layers and then stop—is not taught or suggested.

Therefore, there exists a need for a tool that reduces the puncture force of a needle, such as a Tuohy needle, and enables a clinician to perform a more controlled entry into the epidural space, thereby reducing the possibility of an accidental dura puncture.

While accidental dura puncture is a concern, simply locating the epidural space may pose a challenge even to the most skilled physicians. Therefore, when a needle such as a Tuohy needle is passed through the ligamentum flavum and into the epidural space, it is helpful for a clinician to receive immediate feedback indicating successful penetration and the location of the tip of the needle. A basic conventional feedback device such as the one in FIG. 2a comprises a needle (not shown) attached to a syringe PA3 at a front portion 9, and wherein the syringe PA3 is formed of a tubular body 10 and houses a biasing element 11 comprising a stem acting as a biasing element. To provide feedback indicating successful epidural penetration the device relies on a biasing force acting against the biasing element 11 which then acts upon a fluid, such as saline or air within the syringe. Essentially, in this hydraulic feedback method, as the biasing force acts upon the fluid, the fluid translates this pressure to an opening of the needle tip. An opposing force, acting on the needle tip as it is held against a tissue such as the ligamentum flavum, acts to prevent the fluid from being released from the syringe. Typically, a clinician's thumbs act as the biasing force source which in turn acts upon the plunger stem. The clinician's thumbs serve to "feel" the hydraulic resistance exerted on the fluid by the opposing tissue force. Upon entering the epidural space, however, the opposing pressure of tissue acting against the tip is removed, and a pressure drop allows the biasing force to move solution out of the syringe through the needle tip. The clinician becomes aware of successful penetration of the epidural space due to his/her thumbs "feeling" the sudden pressure drop or loss of resistance at the plunger stem. Also, the clinician may receive visual indication of successful penetration by witnessing the plunger advancing through the syringe externally as the fluid is released into the epidural space in the patient. One problem with this conventional device and method is that it is difficult for a clinician to both apply a biasing force on the plunger while also applying an advancing force against the syringe body in order to advance the needle through the ligamentum flavum. Moreover, to prevent accidental dura puncture, clinicians tend to hold the conventional syringe in such a way as to hold the patient steady, while applying a forward momentum against the syringe, and while applying a biasing force against the plunger stem. This is both awkward and uncomfortable to the clinician and patient.

Some advancements have also attempted to provide an automatic biasing element to act against the plunger of an epidural syringe while also providing visual indication or feedback, rather than tactile response, of successful puncture of various internal target areas in the human body. For example, in U.S. Patent Publication No. 2007/0142766 (Sundar et al.), a spring is utilized to act with a biasing force against the syringe plunger. When the epidural needle attached to the syringe passes through into the dural space, the pressure drop allows the spring to bias the plunger. As the plunger moves, the stem provides at least some visual indication as it moves with the plunger. Similarly, U.S. Pat. No. 5,024,662 (Menes et al.), which is hereby incorporated by reference, provides visual indication by utilizing an elastomer band to provide the biasing force against the plunger stem. In U.S. Pat. No. 4,623,335 (Jackson) which is hereby incorporated by reference, an alternative device assists in visually indicating a pressure to identify the location of the needle tip. In addition, U.S. Pat. No. 7,297,131 (Call) which is hereby incorporated by reference, uses a pressure transducer to translate a pressure change into an electronic signal. The electronic signal is then converted to a visual display indicator, for example by activating a light emitting diode to emit.

Therefore, a need exists to overcome the challenges not addressed by conventionally available technologies that reduces the force necessary for penetration of a sharp medical element of a medical device through tissue and also has the ability to deliver (e.g., deliver saline solution, or drugs, etc.) or retrieve materials subcutaneously (e.g., bone biopsy, etc.).

A need also exists to provide visual, tactile, electrical or additional indication to a clinician that the penetrating member has successfully penetrated the specific body space such as the epidural space, especially when the force to enter such a space has been substantially reduced. And this same force reduction must be either controlled or shut off immediately upon entry into the epidural space to avoid (easier) penetration of the dura.

Specifically, a need exists in the medical device art for an improved medical device having a penetrating element that is vibrated at a frequency that thereby reduces the force required to penetrate tissue, reduces the amount of resulting tissue damage and scarring, improving body space or vessel access success rate, minimizes introduction wound site trauma and, most importantly, improves patient comfort while minimizing potential complications.

A need exists for a clinician to be able to use less force to penetrate hard tissue such as the cortical bone during bone biopsy, which would reduce clinician fatigue, patient discomfort, and tissue damage while improving the sampling success rate and quality. There is a need to sense proper location, stop forward motion and collect the sample. There is a further need to turn device on after collection and to reduce force and patient discomfort as the penetrating member is being retracted from the body.

There is also a need for spinal access procedures where a clinician would want a reduction of force as well as to know the location of the needle tip but applied to a relatively-sharp penetrating member, such as a pencil point tip, as the clinician does not want to core tissue.

There is also a need for performing nerve block procedures where a clinician would want a reduction of force as well as to know the location of the needle tip. And this same force reduction must be either controlled or shut off immediately upon entry into the desired location.

All references cited herein are incorporated herein by reference in their entireties.

SUMMARY OF THE INVENTION

The basis of the invention is a handheld medical device, (e.g., epidural needle, bone biopsy device, spinal needle, regional block needle, catheter introducer needle, etc.) having a penetrating member (e.g., an introducer needle, Tuohy needle, pencil point tipped needle, trocar needle (e.g., JAMSHIDI® biopsy needle), etc.), at a distal end, for use in procedures, (e.g., vascular entry and catheterization, single shot or continuous epidurals, spinal access, regional blocks, or bone biopsy, etc.), wherein the medical device comprises at least one driving actuator, (e.g., a piezoelectric, voice coil, solenoid, pneumatic, fluidic or any oscillatory or translational actuator etc.) attached to the penetrating member (e.g., at a proximal end of the penetrating member), and wherein the driving actuator translates the penetrating member, causing it to reciprocate at small displacements, thereby reducing the force required to penetrate through tissues.

Additionally, the invention comprises a means for providing feedback, either visually, audibly, or by tactile response, using a variety of detection mechanisms (such as, but not limited to, electrical, magnetic, pressure, capacitive, inductive, etc. means), to indicate successful penetration of various tissues, or of voids within the body such as the epidural space so that the clinician knows when to stop as well as to limit power to the driving mechanism.

Actuator technologies that rely on conventional, single or stacked piezoelectric material assemblies for actuation are hindered by the maximum strain limit of the piezoelectric materials themselves. Because the maximum strain limit of conventional piezoelectric materials is about 0.1% for polycrystalline piezoelectric materials, such as lead zirconate titanate (PZT) polycrystalline (also referred to as ceramic) materials and 0.5% for single crystal piezoelectric materials, it would require a large stack of cells to approach useful displacement or actuation of, for example, a handheld medical device usable for processes penetrating through tissues. However, using a large stack of cells to actuate components of a handpiece would also require that the tool size be increased beyond usable biometric design for handheld instruments.

Flextensional actuator assembly designs have been developed which provide amplification in piezoelectric material stack strain displacement. The flextensional designs comprise a piezoelectric material driving cell disposed within a frame, platen, endcaps or housing. The geometry of the frame, platten, endcaps or housing provides amplification of the axial or longitudinal motions of the driver cell to obtain a larger displacement of the flextensional assembly in a particular direction. Essentially, the flextensional actuator assembly more efficiently converts strain in one direction into movement (or force) in a second direction. Flextensional piezoelectric actuators may be considered mid-frequency actuators, e.g., 25-35 kHz. Flextensional actuators may take on several embodiments. For example, in one embodiment, flextensional actuators are of the Cymbal type, as described in U.S. Pat. No. 5,729,077 (Newnham), which is hereby incorporated by reference. In another embodiment, flextensional actuators are of the amplified piezoelectric actuator ("APA") type as described in U.S. Pat. No. 6,465,936 (Knowles), which is hereby incorporated by reference. In yet another embodiment, the actuator is a Langevin or bolted dumbbell-type actuator, similar to, but not limited to that which is disclosed in U.S. Patent Application Publication No. 2007/0063618 A1 (Bromfield), which is hereby incorporated by reference.

In a preferred embodiment, the present invention comprises a handheld device including a body, a flextensional actuator disposed within said body and a penetrating or "sharps" member attached to one face of the flextensional actuator. In the broadest scope of the invention, the penetrating member may be hollow or solid. The actuator may have an internal bore running from a distal end to a proximal end or may have a side port located on the penetrating member attachment fitting. Therefore for single use penetrating members there is no need to sterilize the penetrating member after use. Where the penetrating member is hollow, it forms a hollow tubular structure having a sharpened distal end. The hollow central portion of the penetrating member is concentric to the internal bore of the actuator, together forming a continuous hollow cavity from a distal end of the actuator body to a proximal end of the penetrating member. For example, the flextensional actuator assembly may utilize flextensional Cymbal actuator technology or amplified piezoelectric actuator (APA) technology. The flextensional actuator assembly provides for improved amplification and improved performance, which are above that of a conventional handheld device. For example, the amplification may be improved by up to about 50-fold. Additionally, the flextensional actuator assembly enables handpiece configurations to have a more simplified design and a smaller format.

One embodiment of the present invention is a resonance driven vascular entry needle to reduce insertion force of the penetrating member and to reduce rolling or collapsing of vasculature.

An alternative embodiment of the present invention is a reduction of force epidural needle that provides the clinician a more controlled entry into the epidural space, minimizing the accidental puncturing of the dural sheath. In this embodiment, an actuator, for example, a Langevin actuator (more commonly referred to as a Langevin transducer), has a hollow penetrating member, for example a hollow needle, attached to a distal portion of the actuator. The Langevin actuator in this embodiment may be open at opposite ends. The openings include a hollow portion extending continuously from the distal end of the actuator to a proximal end of the actuator. The distal opening coincides with the hollow penetrating member. A plunger, having a handle, a shaft and a seal is also attached to the actuator at an opposite end of the sharps member. The plunger's shaft is slidably disposed within the continuous, hollowed inner portion of the actuator. The seal is attached to a distal portion of the plunger's shaft and separates a distal volume of the hollowed inner portion of the actuator from a proximal volume of the hollowed inner portion. Because the plunger's shaft is slidably disposed, the plunger is also slidably disposed and, in response to a motion of the shaft in a distal direction, reduces the distal volume of the hollowed inner portion and increases the proximal volume. Conversely, in response to a motion of the shaft in a proximal direction, the seal also moves in a proximal direction, thereby reducing the proximal volume of the hollowed portion and increasing the distal volume. The motion of the plunger's shaft, and, effectively, the plunger's seal, is actuated by an external force acting on the plunger's handle. When electrically activated, the actuator transfers compression and expansion of the piezoelectric material portion to a hollow and penetrating tip of the hollow needle. Langevin actuators may be considered high frequency actuators, e.g., >50 kHz.

Another embodiment of the invention provides a bone marrow biopsy device having an outer casing, an actuator, for example, a Langevin actuator (e.g., see, for example, U.S. Pat. No. 6,491,708 (Madan, et al.), whose entire disclosure is incorporated by reference herein), including a first body portion and a second body portion of the actuator, with piezoelectric material formed between the first and second body portions, wherein the actuator is disposed at least partially within the casing. The invention further includes a handle, an outer cannula, such as a needle, having an open distal end and an open proximal end with the cannula positioned at a distal portion of the actuator. In one aspect of the present embodiment, the invention further comprises a stylet having a penetrating distal tip attached to the handle at a portion opposite the distal tip, wherein the stylet is slidably disposed through a center cavity of the body and cannula. The actuator is formed with a distal opening formed at a distal end of the actuator, and a proximal opening formed at a proximal end of the actuator with a centralized hollow bore extending from the distal opening to the proximal opening, thereby defining a hollow channel.

More precisely, the outer cannula is a hollow tube fixedly attached at the distal end of the actuator such that the open proximal end of the cannula coincides with the distal opening of the actuator distal end. The stylet is slidably and centrally disposed within the actuator from the proximal end through the hollow channel and through the distal end. The stylet is also of predetermined length such that it is slidably and centrally located through the outer cannula, with the distal tip of the stylet protruding past the open distal end of the cannula.

The various actuators of the present invention must be connected electrically to an external electrical signal source. Upon excitation by the electrical signal, the actuators convert the signal into mechanical energy that results in vibratory motion of an end-effector, such as an attached needle or stylet. In the case of a Langevin actuator, the vibratory motion produced by the piezoelectric materials generates a standing wave through the whole assembly such as that in graph in FIG. 17. Because at a given frequency, a standing wave is comprised of locations of zero-displacement (node, or zero node) and maximum displacement (anti-node—not shown) in a continuous manner, the displacement that results at any point along the actuator depends on the location where the displacement is to be measured. Therefore, the horn is typically designed with such a length so as to provide the distal end of the horn at an anti-node when the device is operated. In this way, the distal end of the horn experiences a large vibratory displacement in a longitudinal direction with respect to the long axis of the actuator. Conversely, the zero node points are locations best suited for adding port openings or slots so as to make it possible to attach external devices to the actuator. As indicated by line ZN, the port opening SP coincides with the zero node location and the smaller displacement at zero node points are less abrasive to an attached device.

Accordingly, an alternative embodiment, the actuator may be formed with a distal opening formed at the distal end of the actuator, a port opening on at least a portion of the actuator, and a hollow bore extending from the distal opening to and in communication with the port opening. Preferably, the port opening may be a side port on a horn side of the actuator. More preferably, the port opening is generally located (preferably centered) at a zero node location of the actuator, and most preferably centered at a zero node location on a horn side of the actuator. Additionally, a means for providing feedback, for example any of those conventional feedback devices disclosed above used for indication of successful body location such as the epidural space penetration is in communication with the present embodiment by attachment at the port opening location, or preferably at the side port. Alternatively, any means capable of delivering fluid, such as a catheter tube or conventional syringe can be attached at the port opening location, or preferably at the side port.

The present invention relates generally to oscillatory or translational actuated handheld device for penetration through various tissues within a body for the delivery or removal of bodily fluids, tissues, nutrients, medicines, therapies, placement or removal of catheters, etc. For example for piezoelectric devices, the present invention is a handpiece including a body, at least one piezoelectric element disposed within the body, and a sharps member for tissue penetration, such as a syringe, epidural needle or biopsy needle located at a distal portion of the handheld device, having a feedback means capable of indicating successful penetration of the body space, such as epidural space by providing visual, audible or tactile indications using any well-known detection mechanisms such as but not limited to electrical, magnetic, pressure, capacitive, inductive, etc. means.

Additionally, with the use of proper circuitry the handheld medical device comprising an actuator is provided with a means for shutting off external power to the driving actuator (e.g., one or more of piezoelectric elements, voice coil, solenoid, other oscillatory or translational actuator, etc.) upon penetration of a particular tissue or internal portion of a body such as the epidural space. The means for shutting off external power to the driving actuator may be implemented as part of the aforementioned means for providing visual, audible or tactile indications or may be a separate means altogether. Preferably the means for shutting off external power to the driving actuator upon penetration of a particular tissue or internal portion of for example, the epidural space, may be accomplished by incorporating proper circuit configurations to aforementioned electrical means to trigger a switching means in order to cut off power to the driving actuator. Such a means is described in U.S. Pat. No. 5,575,789 (Bell et al.) whose entire disclosure is incorporated by reference herein. By providing such electrical cut-off means, upon successfully penetrating the epidural space for example, a clinician receives one or more of a visual, audible, and tactile indications as well as a loss of power to the device as a secondary indication that a particular internal portion of a body has been penetrated. Furthermore, with a loss of power to the device by cutting off electrical power to the driving actuator, the force or forward momentum necessary for further penetration of tissue will cease and in turn, will decrease the potential for unwanted body area puncture such as accidental dural puncture.

Additionally the invention with specific control electronics will provide reduction of force as the penetrating member is retracted from the body.

In one embodiment, the penetrating or sharp tubular member is part of a vascular entry needle.

In another embodiment, the penetrating sharp tubular member is a Tuohy needle.

In yet another embodiment, the penetrating or sharp tubular member is a trocar and stylet assembly, such as a JAMSHIDI® biopsy needle.

In yet another embodiment, the penetrating or sharp tubular member is a pencil point tipped needle.

In yet another embodiment, the penetrating or sharp tubular member is part of a trocar access port.

These and other features of this invention are described in, or are apparent from, the following detailed description of various exemplary embodiments of this invention.

BRIEF DESCRIPTION OF THE DRAWINGS

Exemplary embodiments of this invention will be described with reference to the accompanying figures.

FIG. 4a is needle design with the side port located in the penetrating member hub providing external access such as for pressure sensor connection or catheter entry location.

FIG. 6a depicts the present invention including a sterilization sleeve for wires and housing;

FIG. 14a is a cross section of the fifth embodiment of the present invention using a penetrating member with side port of FIG. 13a;

FIG. 16 is a cross section of the sixth embodiment of the present invention using the penetrating member with side port of FIG. 13a;

FIG. 18d is a sketch of a eighth embodiment of the present invention comprising the side port connected to the short bore and communication with needle attachment that is also connected to the front portion of the Langevin actuator and without the handle shown of the actuator of FIG. 18a;

FIG. 20b is a cross-sectional view of the tenth embodiment of the present invention using a voice coil for the driving actuator wherein the position of the magnetic member and the coil are reversed from that of FIG. 20a;

BRIEF DESCRIPTION OF THE INVENTION

Figure 1:
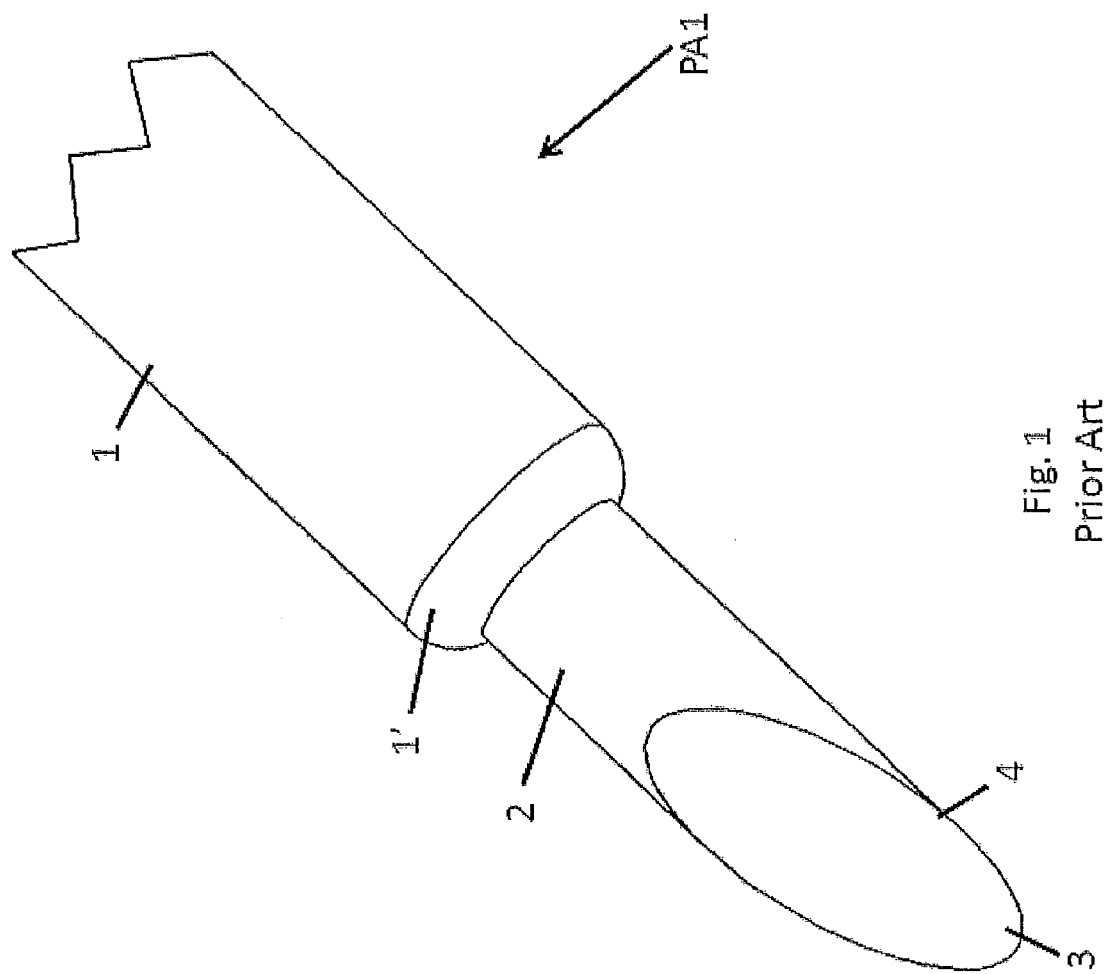
FIG. 1 is a partial isometric view of a distal end of a prior art biopsy needle.
Figure 2:
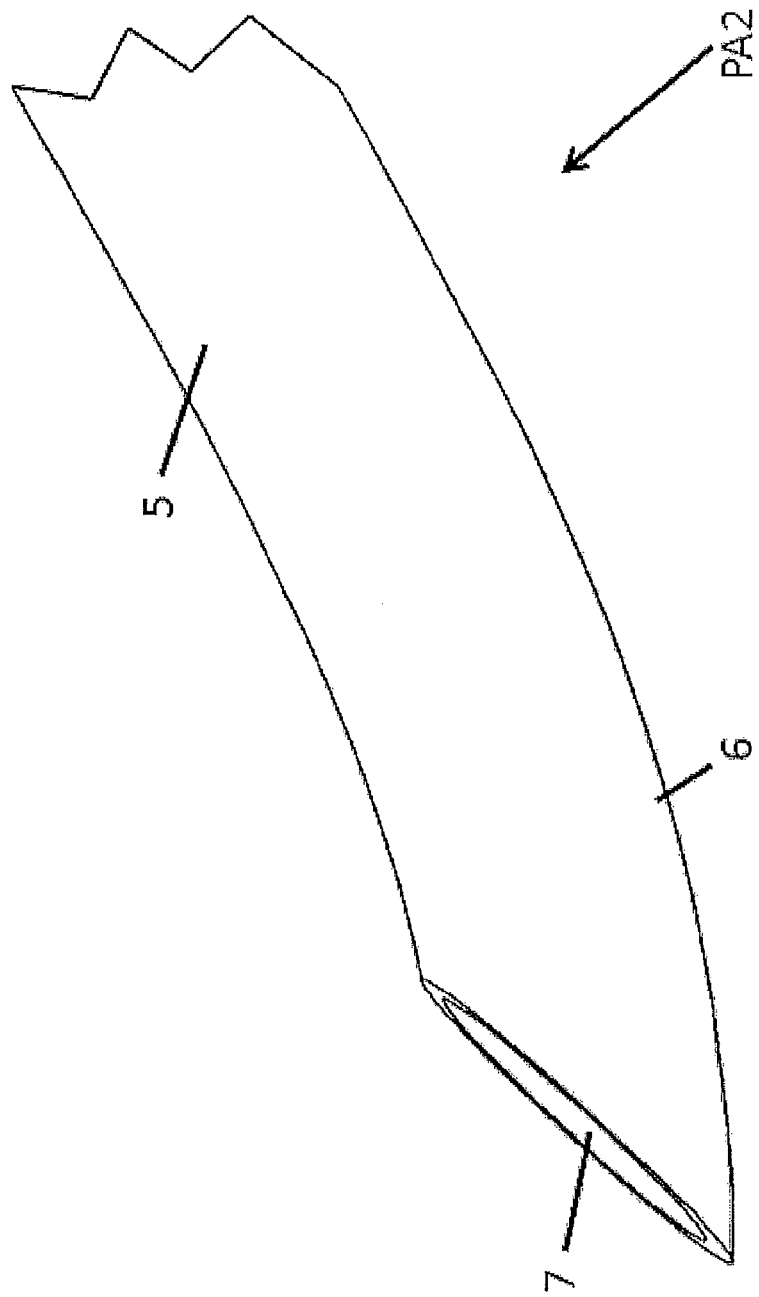
FIG. 2 is a partial side view of a distal end of a prior art epidural needle.
Figure 2A:
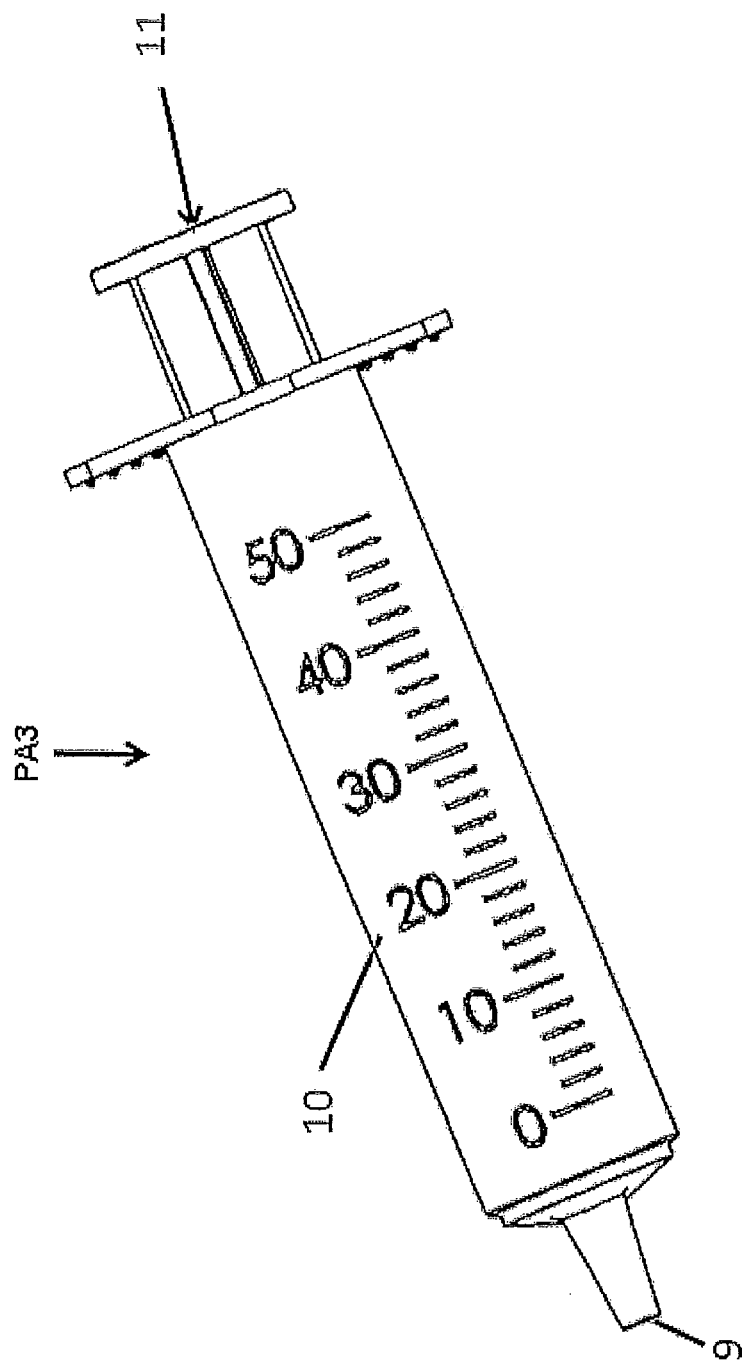
FIG. 2a is a plan view of a conventional prior art loss of resistance syringe.

The preferred embodiments of the present invention are illustrated in FIGS. 3-21 with the numerals referring to like and corresponding parts. For purposes of describing relative configuration of various elements of the invention, the terms "distal", "distally", "proximal" or "proximally" are not defined so narrowly as to mean a particular rigid direction, but, rather, are used as placeholders to define relative locations which shall be defined in context with the attached drawings and reference numerals. A listing of the various reference labels are provided at the end of this Specification. In addition, U.S. application Ser. No. 12/163,071 entitled "Medical Tool for Reduced Tool Penetration Force," filed on Jun. 27, 2008 is incorporated by reference in its entirety.

The effectiveness of the invention as described, for example, in the aforementioned preferred embodiments, utilizes reduction of force to optimize penetrating through tissue or materials found within the body. Essentially, when tissue is penetrated by the high speed operation of a penetrating member portion of the device, such as a needle, the force required for entry is reduced. In other words, a reduction of force effect is observed when a penetrating member (also referred to as a "tubular member"), for example a needle, is vibrated axially (e.g., reciprocated) during the insertion process and enough mechanical energy is present to break adhesive bonds between tissue and the penetrating member. The threshold limits of energy can be reached in the sonic to ultrasonic frequency ranges if the necessary amount of needle displacement is present.

To exploit the reduction of force effect, the medical device of the present invention is designed such that the penetrating distal tip portion attains a short travel distance or displacement, and vibrates sinusoidally with a high penetrating frequency. Utilizing the various device configurations as described in the aforementioned embodiments, it has been determined that the sinusoidal motion of the sharp distal tip must include a displacement for piezoelectric tools of between 35-100 µm, more preferably between 50-100 µm, at a frequency of between 20-50 kHz, but most preferably at 20-25 kHz. This motion is caused by the penetrating member 20 being attached to an actuating piezoelectric actuator operated at 50-150 Vpp/mm, but most preferably at 90 Vpp/mm where Vpp is known as the peak-to-peak voltage.

Figure 3:
FIG. 3 is a graph illustrating the penetration force of a penetrating member.

For example, FIG. 3 shows a graphical representation of the resisting force versus depth of a bone biopsy needle penetrating into hard tissue. In FIG. 3, the curve labeled A represents data for a needle in an "off" or non-vibrating condition and the curve labeled B represents data for a medical device having a needle that is vibrated by a piezoelectric actuator at 38 kHz and a displacement of 100 μm. As apparent from FIG. 3, curve A shows that without being vibrated, the force necessary to penetrate into a material is much higher than that for a needle being oscillated, such as that represented by curve B.

Figure 4:
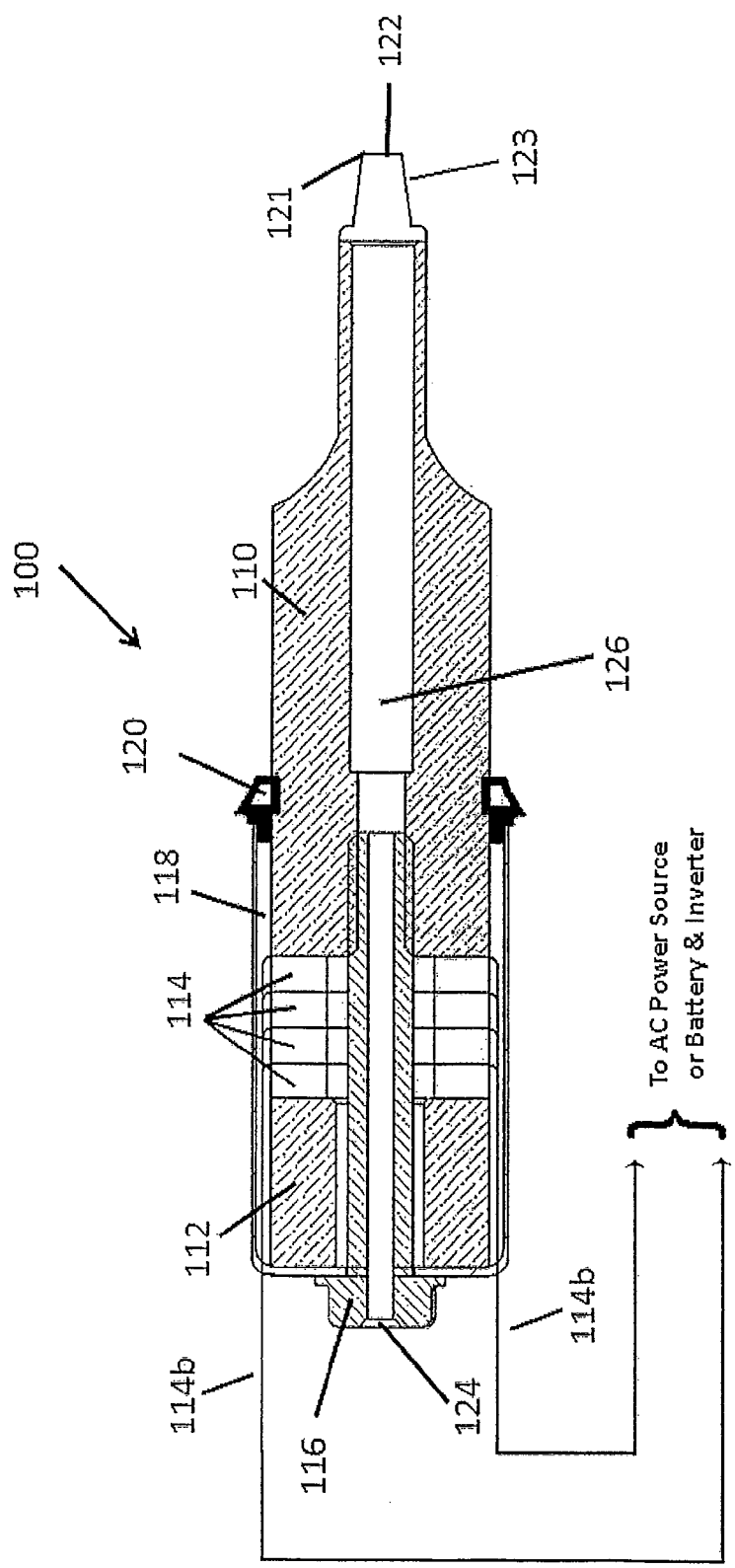
FIG. 4 is a cross section of a Langevin actuator, more commonly referred to as a Langevin transducer, for use as an actuator in a first embodiment of the present invention.

By way of example only, referring to FIG. 4, a Langevin actuator, generally indicated as 100, comprises a piezoelectric actuator which includes a body having a central hollow channel and includes a displaceable member (also referred to as a "horn") 110, an anchor (also referred to as a "rear mass") 112 and at least one piezoelectric element 114, but preferably comprises more than one. In particular, each piezoelectric element 114 may be formed into a piezoelectric ring that forms a hollow portion and wherein the piezoelectric elements 114 are secured within the body and attached between horn 110 and rear mass 112. A hollow or solid threaded bolt 116 is disposed within a center portion of rear mass 112, extending through a center portion of the at least one of piezoelectric elements 114 and ending within a central portion of horn 110. The bolt compresses the rear mass 112, the at least one of piezoelectric elements 114 and horn 110. The horn 110 and rear mass 112 are made of a metal such as titanium, stainless steel, ceramic (which include polycrystalline and single crystal inorganic materials), plastic, composite or, preferably, aluminum. The bolt 116 is of the same material as the horn 110 and rear mass 112. To protect patient and clinician from electric shock, at least a portion of the Langevin actuator 100, preferably at least the whole of the rear body 112, all of the at least one piezoelectric elements 114, and at least a portion of the horn 110, are disposed within a handle 118. Electrical connection is made at metallic tabs (not shown) formed between opposing faces of the at least one of piezoelectric elements 114. These tabs can be coupled via electrical conductors 114*b* connected to an AC power source or battery (e.g., positioned within a battery compartment of the present invention). The handle 118 comprises a shell portion which may be a plastic or a metal and a seal 120 which may be an elastomer. Seal 120 prevents moisture from entering or exiting from the central portions of the rear mass 112, piezoelectric elements 114 and horn 110. The central portion of the rear mass 112, piezoelectric elements 114 and horn 110 coincide with the hollow portion of the bolt 116 forming a continuous bore 126 within the Langevin actuator 100, the bore 126 having a distal opening 122 at a distal face 121 and a proximal opening 124 at a face opposite to the distal face 121. A Luer taper nose 123 is added to the actuator for clarity of connection.

It should be understood that the number of piezoelectric elements 114 does not form a limitation on the present invention and that it is within the broadest scope of the present invention to include one or more piezoelectric elements 114.

According to an alternative embodiment, a side port (not shown) may be formed at the horn 110 side of the actuator and the continuous bore 126 extends from a distal opening 122 at distal face 121 and in communication with this side port. The functional performance of the medical device is driven by the piezoelectric elements section. Piezoelectric elements 114, such as each of one or more piezoelectric material rings are capable of precise, controlled displacement and can generate energy at a specific frequency. The piezoelectric materials expand when exposed to an electrical input, due to the asymmetry of the crystal structure, in a process known as the converse piezoelectric effect. Contraction is also possible with negative voltage. Piezoelectric strain is quantified through the piezoelectric coefficients $d_{33}$, $d_{31}$, and $d_{15}$, multiplied by the electric field, E, to determine the strain, x, induced in the material. Ferroelectric polycrystalline materials, such as barium titanate (BT) and lead zirconate titanate (PZT), exhibit piezoelectricity when electrically poled. Simple devices composed of a disk or a multilayer type directly use the strain induced in a material by the applied electric field. Acoustic and ultrasonic vibrations can be generated by an alternating field tuned at the mechanical resonance frequency of a piezoelectric device. Piezoelectric components can be fabricated in a wide range of shapes and sizes. In one embodiment, piezoelectric component may be 2-5 mm in diameter and 3-5 mm long, possibly composed of several stacked rings, disks or plates. The exact dimensions of the piezoelectric component are performance dependent. The piezoelectric single or polycrystalline materials may be comprised of at least one of lead zirconate titanate (PZT), multilayer PZT, lead magnesium niobate-lead titanate (PMN-PT), multilayer PMN-PT, lead zinc niobate-lead titanate (PZN-PT), polyvinylidene difluoride (PVDF), multilayer PVDF, and other ferroelectric polymers. These materials also can be doped which changes properties and enhances the performance of the medical device. This list is not intended to be all inclusive of all possible piezoelectric materials. For example there is significant research into non-lead (Pb) containing materials that once developed will operate in this invention.

In the embodiment shown in FIG. 4*a* the side port SP is located on the penetrating member hub 525 of the hollow needle 130. In this alternate embodiment the hollow needle 130 penetrating member hub 525 is preferably metal or a combination of metal insert molded in a plastic. The side port SP would contain a female Luer taper opening to attach a loss of resistance conventional syringe PA3.

Figure 5:
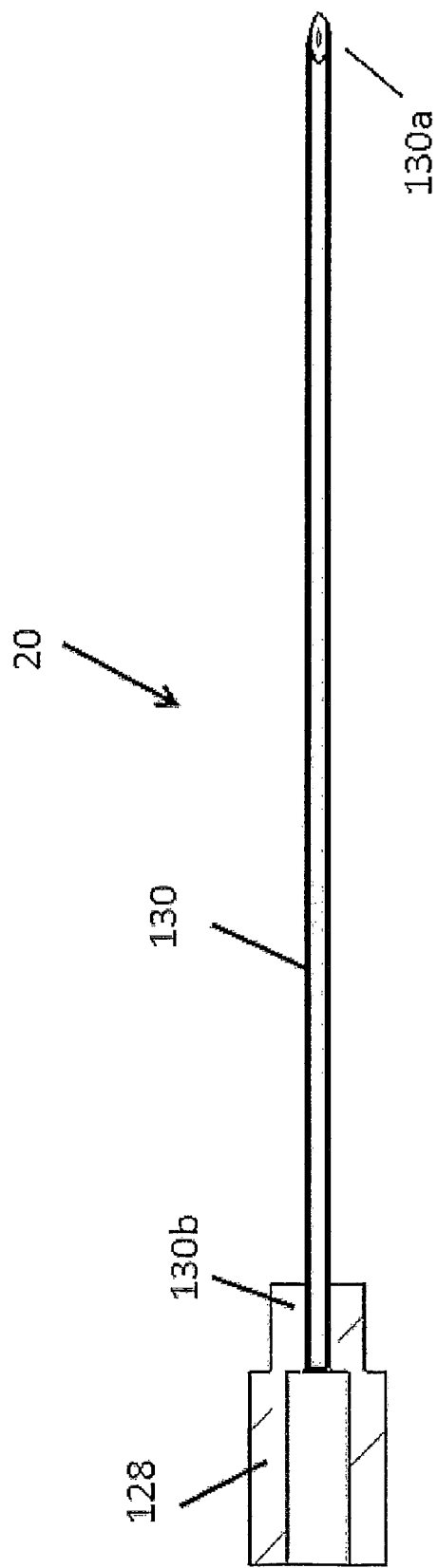
FIG. 5 is a cross section of a vascular entry needle used in a first embodiment of the invention.

Referring now to FIG. 5, a penetrating member, generally indicated as 20, for use in a first embodiment of the present invention comprises an attachment fitting 128 connected to proximal end 130*b* and the distal end 130*a* of a hollow needle 130 penetrates tissue. By way of example only, the attachment fitting 128 may comprise a Luer taper, plastic or metal fitting.

Figure 6:
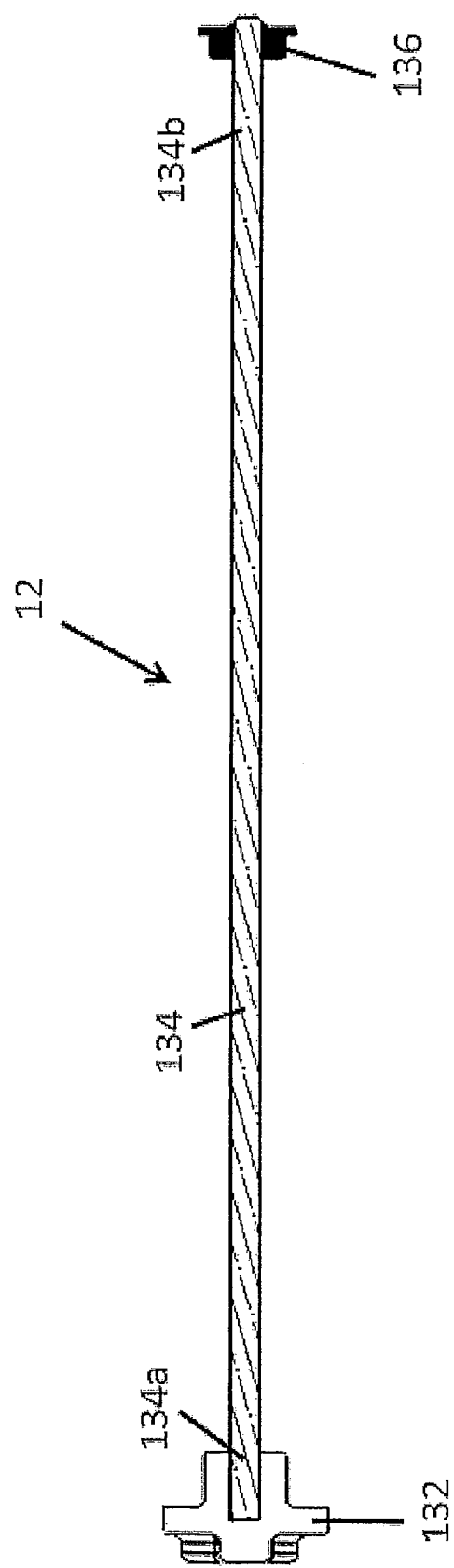
FIG. 6 is a cross section of a plunger used in a first embodiment of the invention.

Referring now to FIG. 6, a plunger 12 for use in a first embodiment of the present invention comprises a plunger handle 132 attached to a proximal end 134*a* of a plunger shaft 134, and a plunger seal 136 attached to a distal end 134*b* of the plunger shaft 134. The plunger seal is used to seal the handle 118 so that contaminates such as water or bodily fluids do not reach the actuator elements or electrical connections. In another embodiment, the plunge will create a vacuum in the hollow penetrating member to aspirate bodily fluids and/or tissue for sampling such as in a soft tissue biopsy procedure.

Figure 6B:
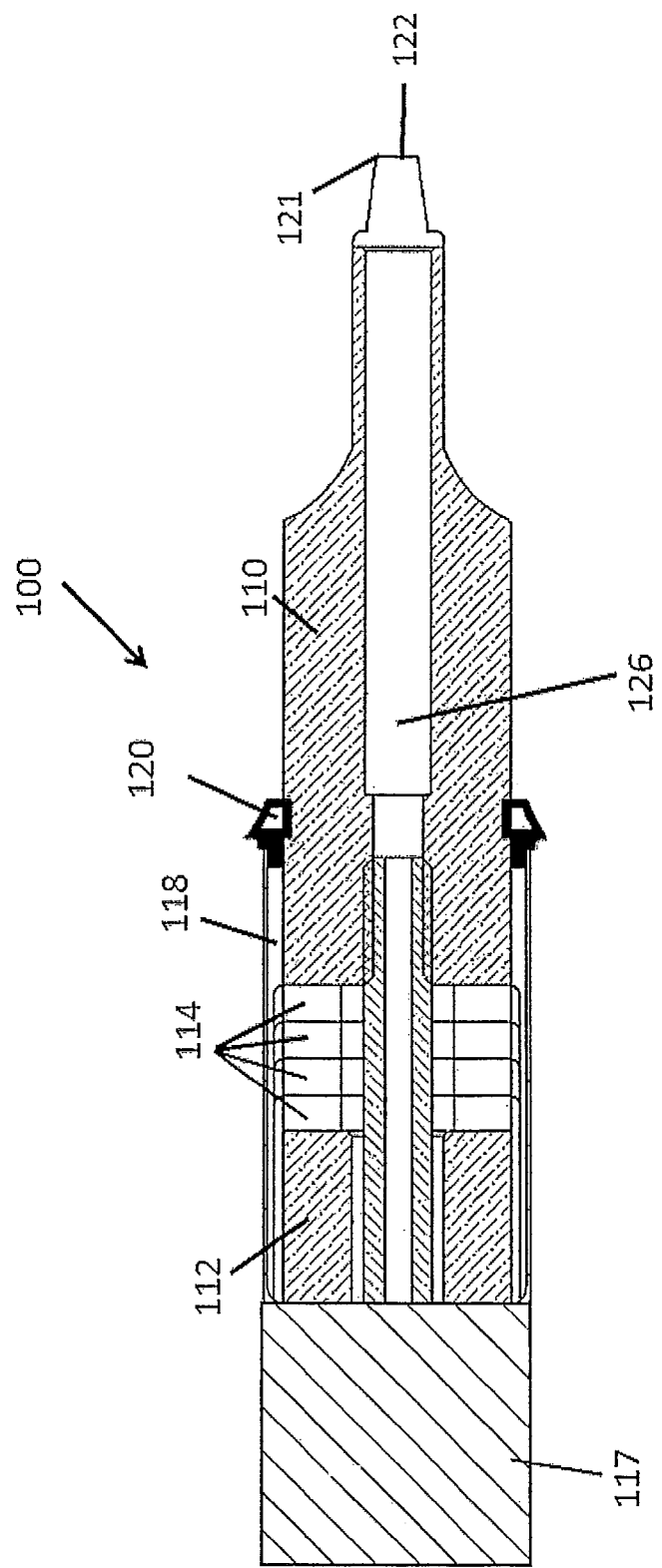
FIG. 6b depicts the present invention including a battery and inverter compartment attached at the end of the actuator.
Figure 7:
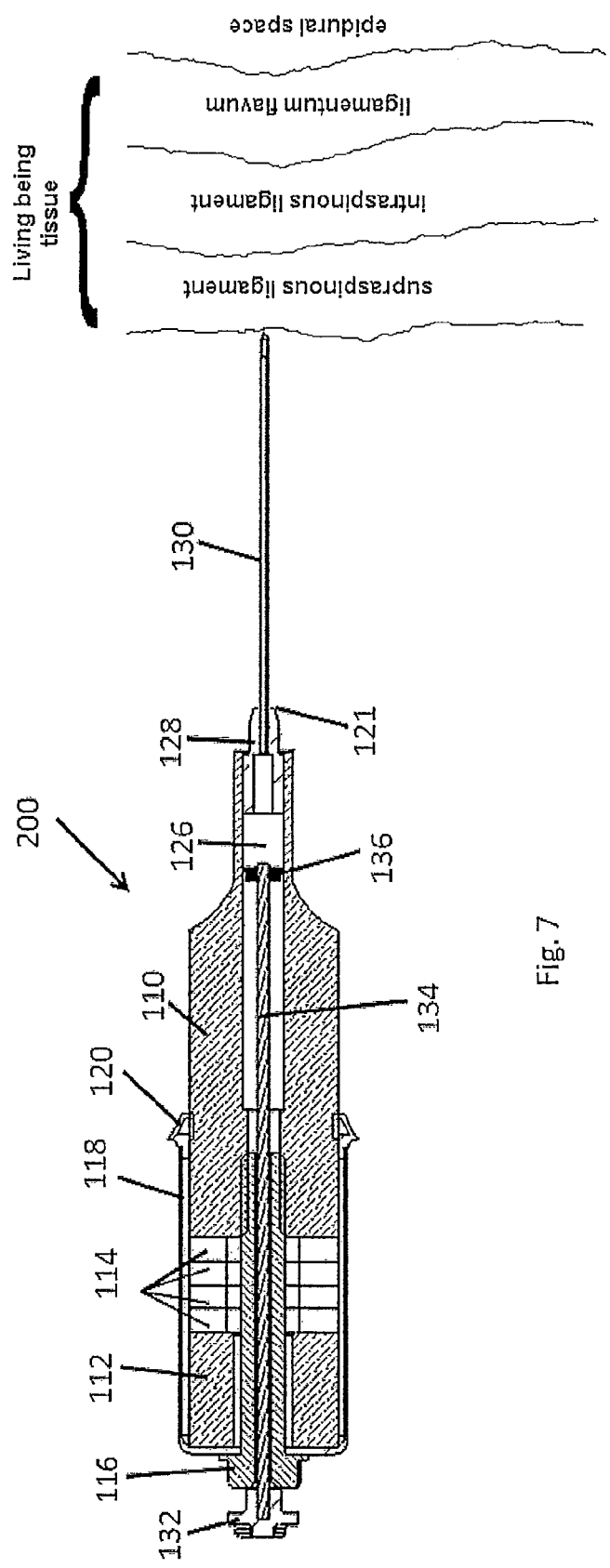
FIG. 7 is a cross section of a first embodiment of the invention.

In the most preferred embodiment, the side port is located on the penetrating member hub 525 at the end attachment point Referring now to FIG. 7, a first embodiment of the present invention, for example a penetrating introducer, generally indicated as 200, comprises an actuator, such as the Langevin actuator 100 described in FIG. 4, with the penetrating member 20 of FIG. 5 being attached at a distal face 121 of the actuator. The needle attachment fitting 128 is a threaded fitting, Luer taper, compression fitting or the like, and couples hollow needle 130 to a portion of distal face 121 such that it communicates with a distal volume of continuous bore 126. Plunger handle 132 may be a threaded, clamped, compressed or the like to bolt 116 so as to immobilize plunger 12 of FIG. 6. The present invention is sterilizable using such methods as steam sterilization, a sleeve, gamma, ethylene oxide (ETO). For example, FIG. 6a depicts a sterilization sleeve 115 for wires and housing used with the present invention. The preferred material for the needle attachment 128 is a metal or a metal insert in a molded plastic. FIG. 6b shows the Langevin actuator 100 with a possible configuration of the battery & inverter compartment 117 attached to the end of the actuator.

Returning to FIGS. 4 and 7, upon application of an external AC current at a predetermined frequency to the at least one of piezoelectric elements 114, the Langevin actuator 100 reactively changes shape in a sinusoidal fashion such that the relative position of distal face 121 with respect to say, a fixed position of plunger handle 132 attached to and held in place by bolt 116, changes by a predetermined displacement. Because the AC current is a sinusoidal signal, the result of activating the piezoelectric elements 114 is a sinusoidal, back and forth motion of the distal face 121 of horn 110, and, subsequently, a back and forth motion of needle 130, thereby reducing the force necessary for penetration through tissue. As mentioned previously, the AC energization can be provided directly from an AC source or from a DC source (e.g., onboard batteries) coupled to an inverter (e.g., oscillator/amplifier, etc.) which in turn is coupled to the piezoelectric elements 114. The DC source is the more preferred embodiment as wires and connections will need additional sterilization features.

Figure 7A:
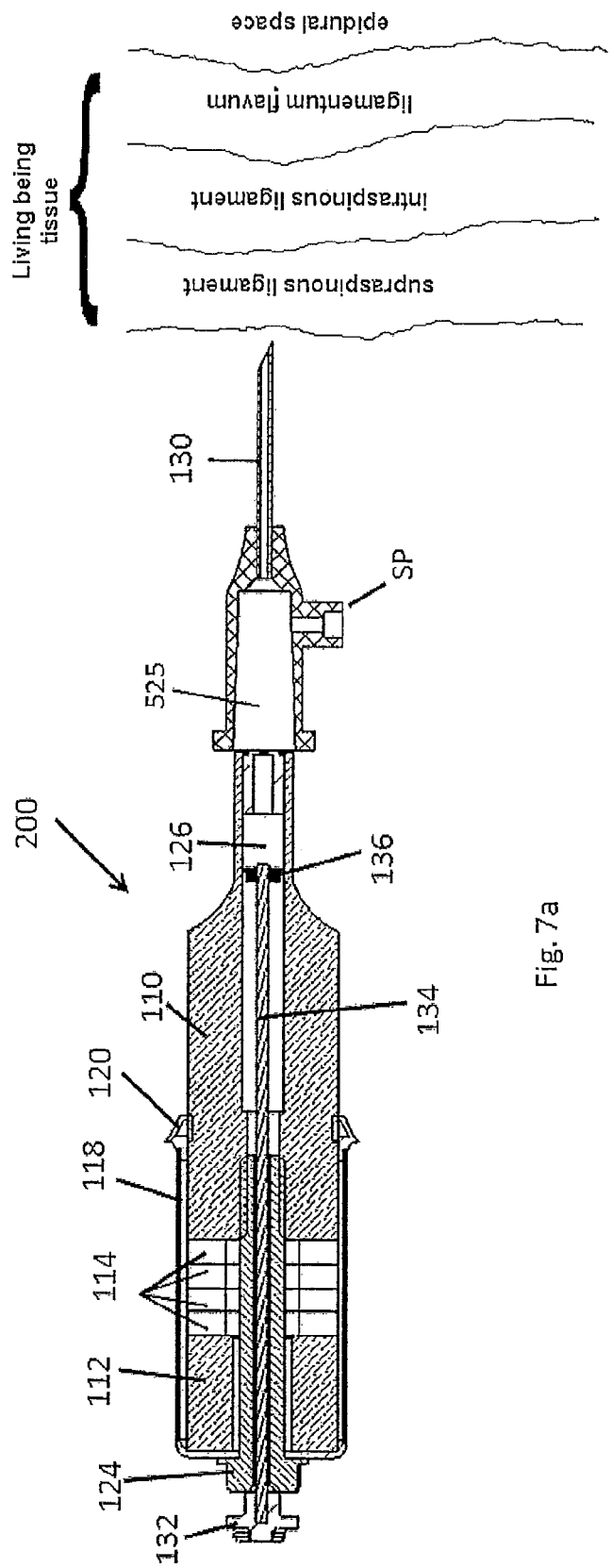
FIG. 7a is a cross-section of an alternate design of the first embodiment of the invention that incorporates the side port on the penetrating member hub.

FIG. 7a depicts a similar invention as shown in FIG. 7 but includes a penetrating member hub 525 with a side port SP connected to the hollow needle 130. This configuration enables pressure sensor to be mounted in the side port SP which once removed provides for a catheter to be inserted or fluids removed. This is likely the preferred embodiment when compared to FIG. 7 as the entire active device will not be at risk for contamination since the catheter or fluids do not traverse the actuator only the hollow needle 130 which could be manufactured for single use.

Figure 8:
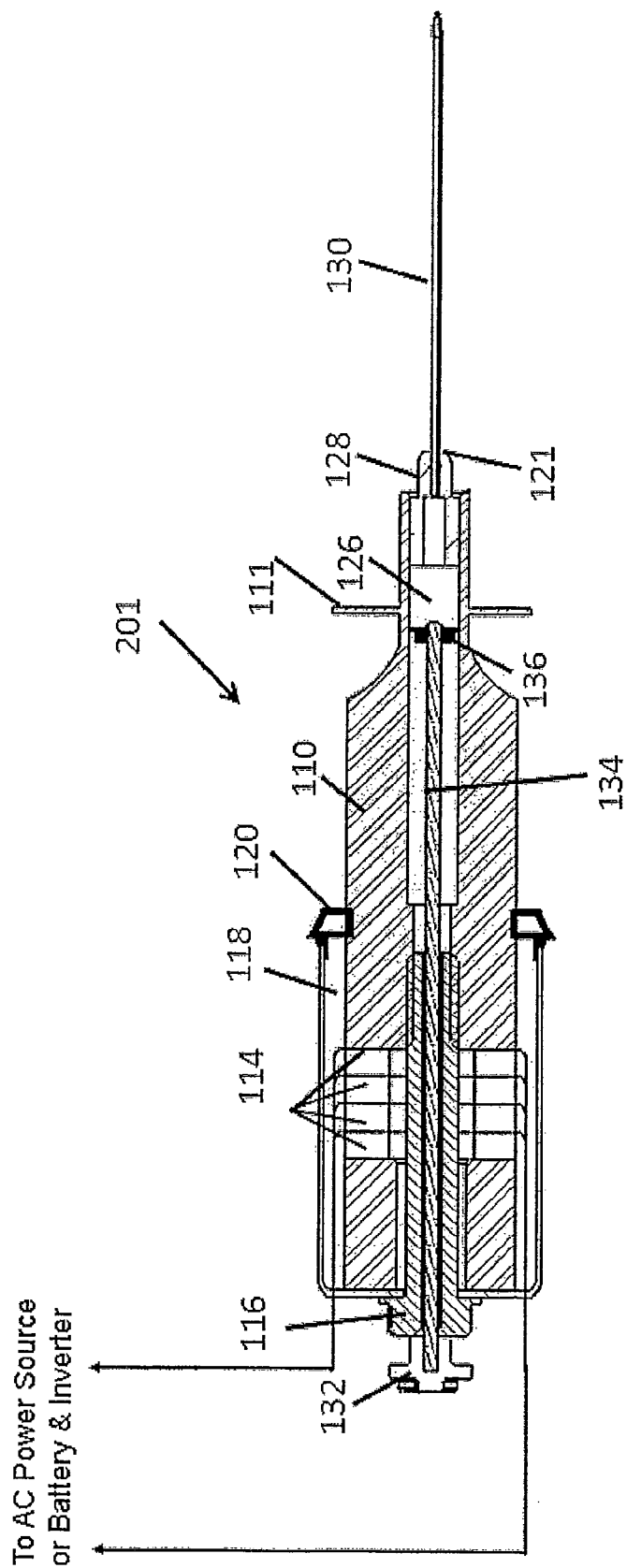
FIG. 8 is a cross section of another alternate design of the first embodiment of the invention of FIG. 7.
Figure 17:
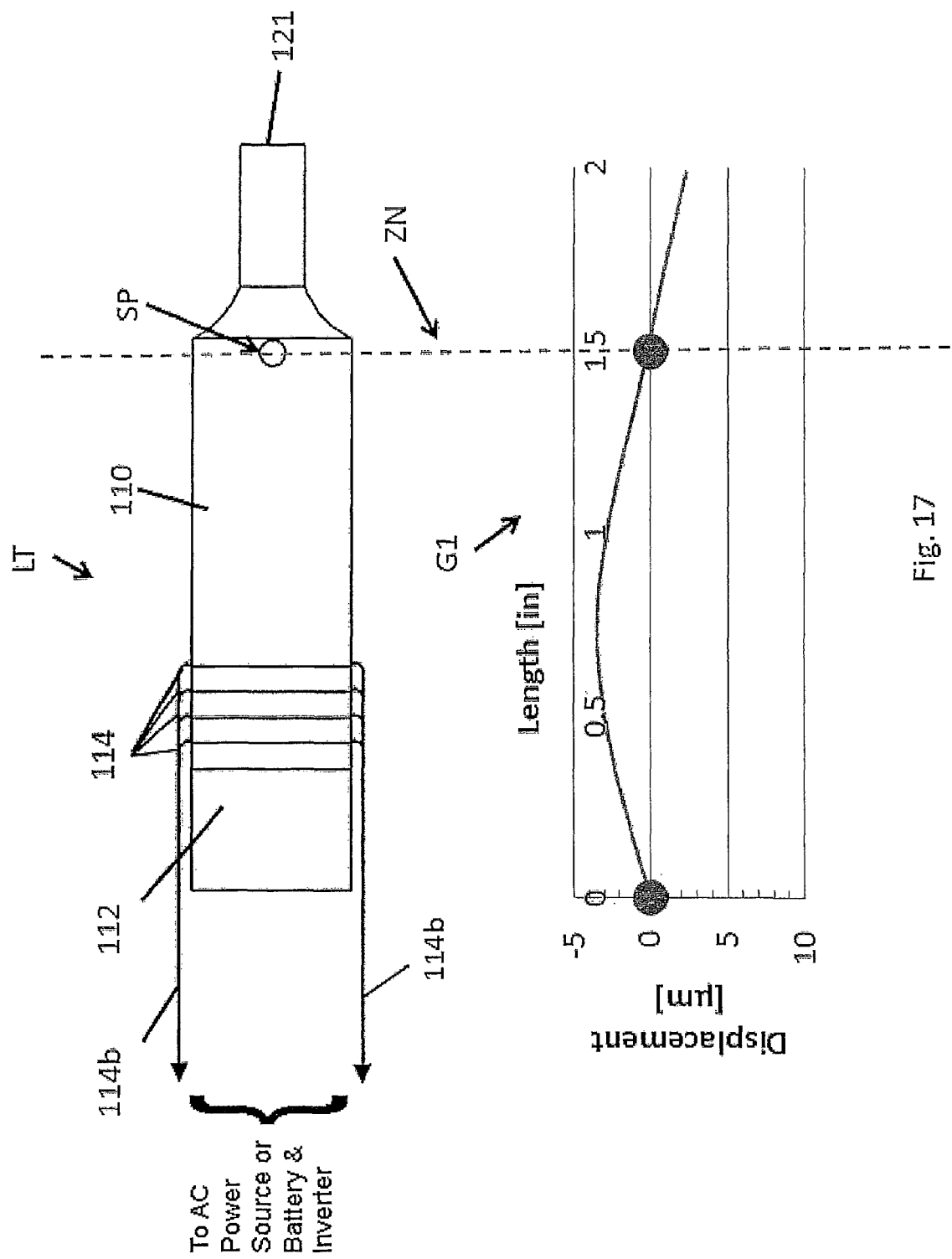
FIG. 17 shows the correlation between zero node points of a standing wave and the location of a side port on a Langevin actuator without the actuator handle shown.

Referring to FIG. 8, a supported introducer, generally indicated as 201, is similar to the penetrating introducer 200 of FIG. 7 additionally comprising support wings 111, existing for example as a flat portion onto which a user can grasp, and extending radially from an outer surface forming a mechanical zero node of the horn 110, as described later with regard to FIG. 17. A side port SP (not shown) could be 90 degrees clockwise or counterclockwise from the support wings that may be a location for providing access for aspirated sample retrieval, catheter insertion etc.

Figure 9:
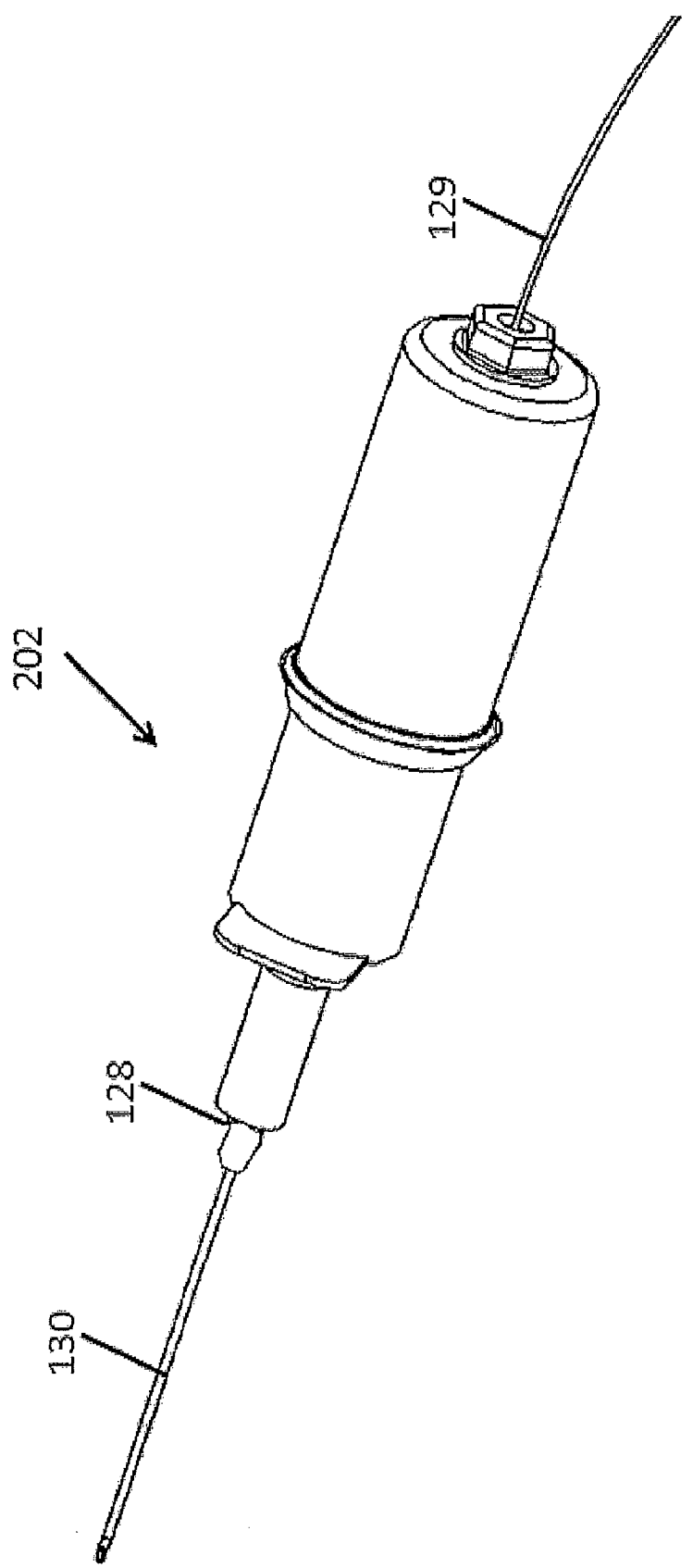
FIG. 9 is an isometric view of a second embodiment of the present invention.

In an alternate embodiment of the present invention, the penetrating introducer 201 of FIG. 8 exists as a catheterization introducer, generally indicated as 202, as shown in FIG. 9. In this embodiment, rather than a plunger being introduced from a proximal end of the device, a catheter 129 is introduced from the proximal end of the device and is received through bore 126 as shown in FIG. 4, and may be passed through hollow needle 130. Upon having been inserted into a patient, hollow needle 130 forms a subcutaneous tunnel through which catheter 129 is introduced into the body. Upon successful introduction, the actuator may be detached from hollow needle 130 by decoupling attachment fitting 128 from the horn 110.

Figure 9A:
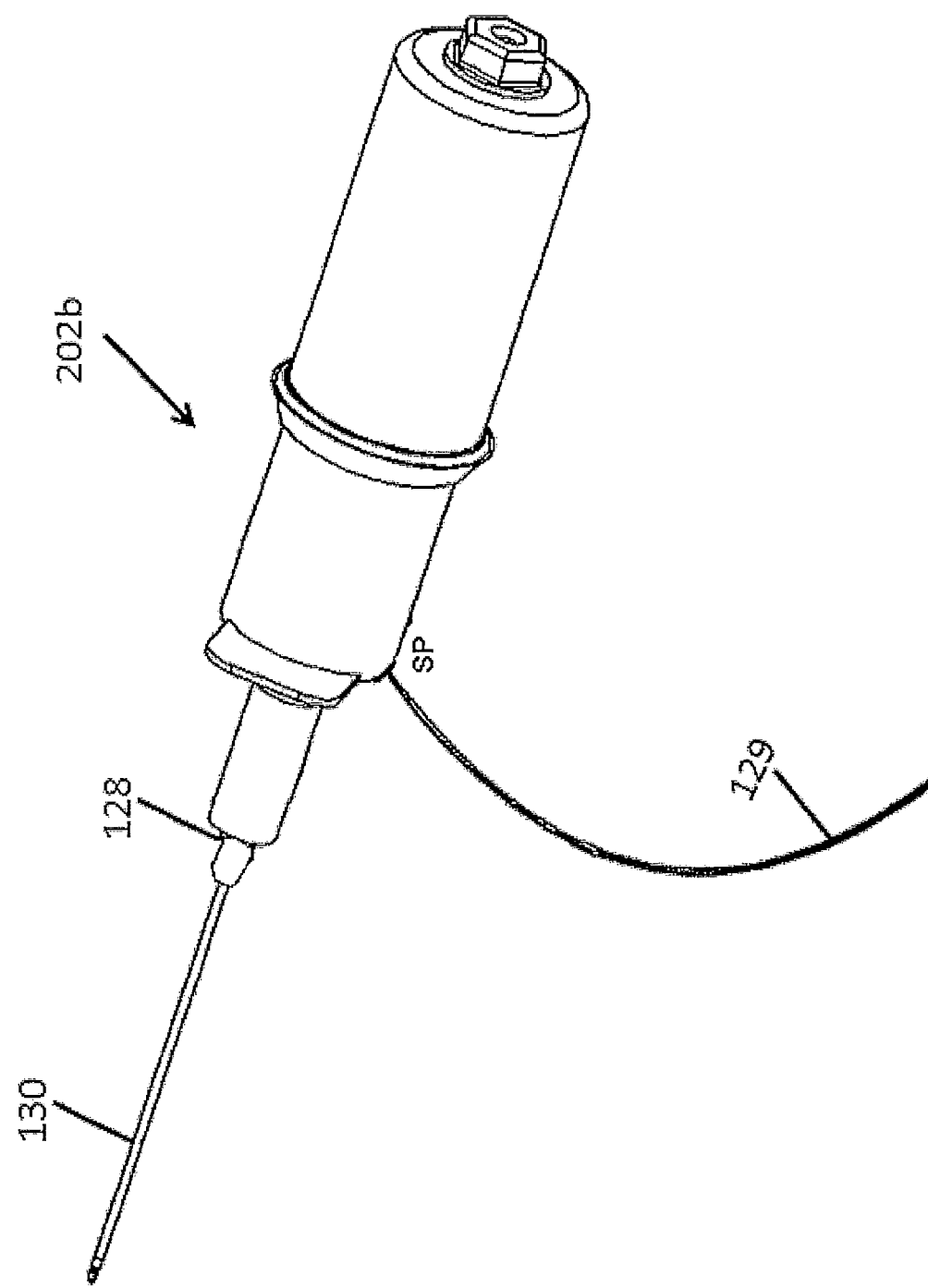
FIG. 9a is an isometric view of an alternate design of the second embodiment using a side port on the actuator for attachment location of the pressure sensor or entry of a catheter.

A more preferred embodiment 202b is shown in FIG. 9a where a side port SP permits the introduction of the catheter 129 into the present invention, rather than through the proximal end, as shown in FIG. 9. This configuration enables pressure sensor to be mounted in the side port SP which once removed enables a catheter to be inserted or fluids removed near the distal face 121 of the device. This is likely the preferred embodiment when compared to FIG. 9 as the entire active device will not be at risk for contamination since the catheter or fluids do not traverse the entire actuator.

Figure 9B:
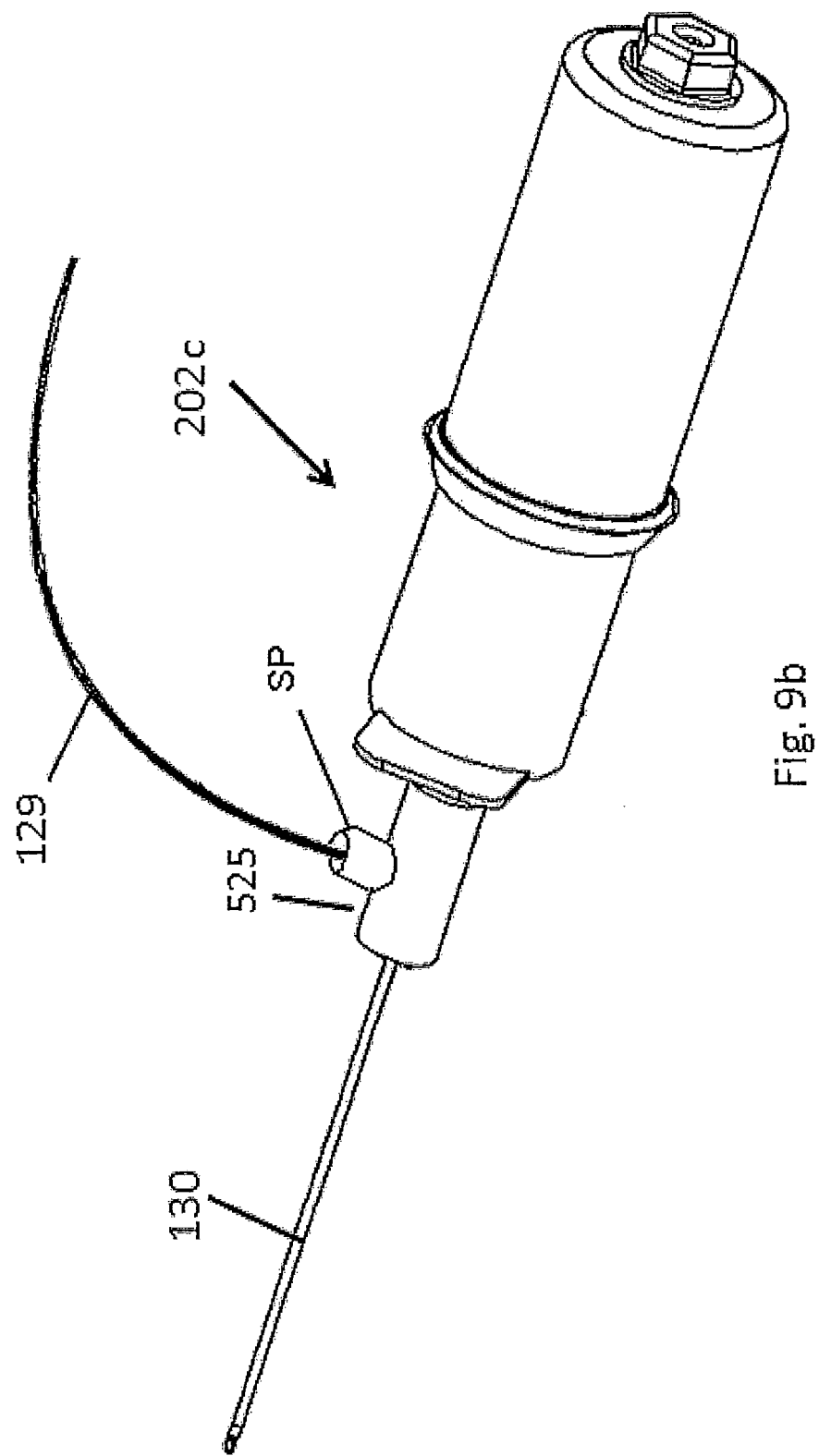
FIG. 9b is an isometric view of more preferred alternate design of the second embodiment using a side port on the penetrating member hub for attachment location of the pressure sensor or entry of a catheter.

In the most preferred embodiment 202c is shown in FIG. 9b where the side port SP located on the penetrating member hub 525 permits a pressure sensor to be mounted in the side port SP which once removed provides entity of an instrument such as a catheter 129 to be inserted or fluids aspirated. This is likely the preferred embodiment when compared to FIG. 9 as the entire active device will not be at risk for contamination since the catheter or fluids do not traverse the actuator only the hollow needle 130.

Figure 10A:
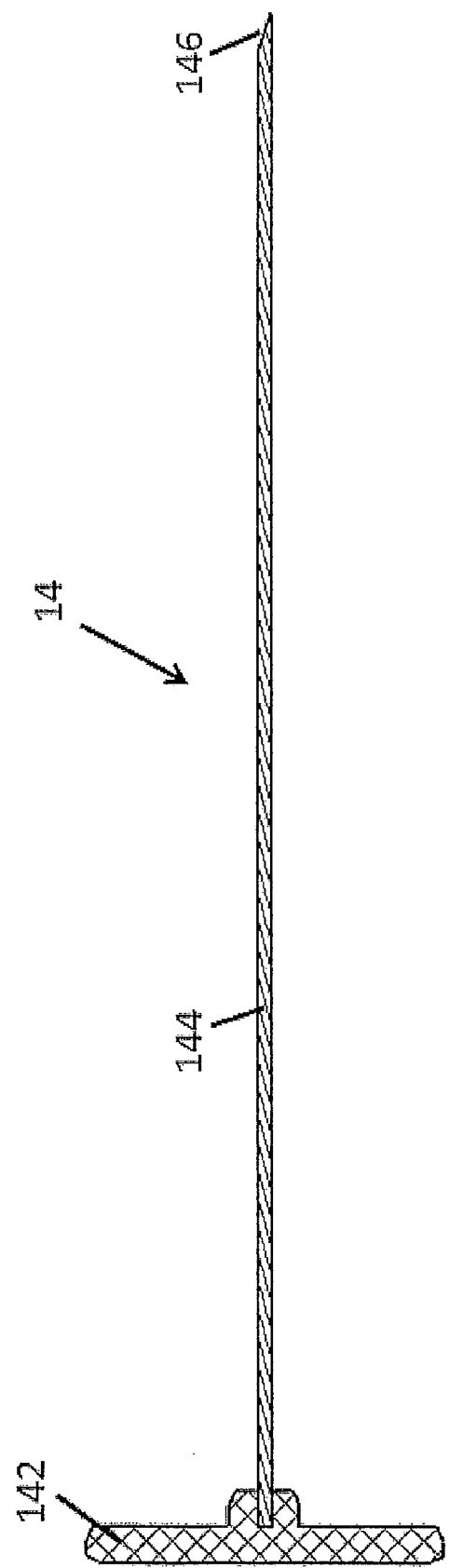
FIG. 10a is a cross section of an inner stylet for use in a third embodiment of the present invention.

Now referring to FIG. 10a, an inner stylet, generally indicated as 14, comprises an inner stylet handle 142 attached to a proximal end of an inner stylet shaft 144. At a distal end of the inner stylet shaft 144, opposite to the handle 142 is a sharpened inner stylet tip 146. To support the inner stylet shaft 144, an outer trocar tube, generally indicated as 15, shown in FIG. 10b comprises a trocar attachment fitting 148 attached at a proximal end of an outer trocar body 150, which is a tubular structure open at opposite ends. The trocar attachment fitting 148 is hollow such that outer trocar body 150 is disposed within it. Additionally, one of the openings formed at opposite ends of the trocar body 150 is a distal trocar opening 152, the outer walls of which form distal trocar tip 154. As shown in FIG. 10c, inner stylet shaft 144 may be slidably disposed within outer trocar body 150 with inner stylet tip 146 extending beyond distal trocar tip 154. Together, the inner stylet 14 of FIG. 10a and outer trocar tube 15 of FIG. 10b form a structure similar to a trocar needle (e.g., a JAMSHIDI® biopsy tool).

Figure 10B:
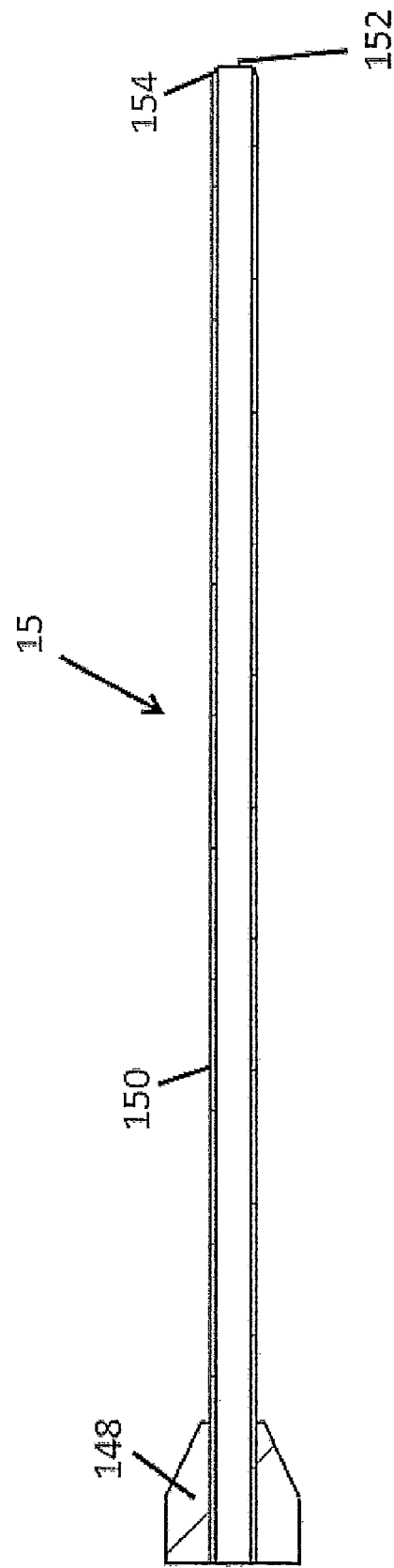
FIG. 10b is a cross section of an outer penetrating member, such as a trocar, for use in a third embodiment of the present invention.
Figure 10C:
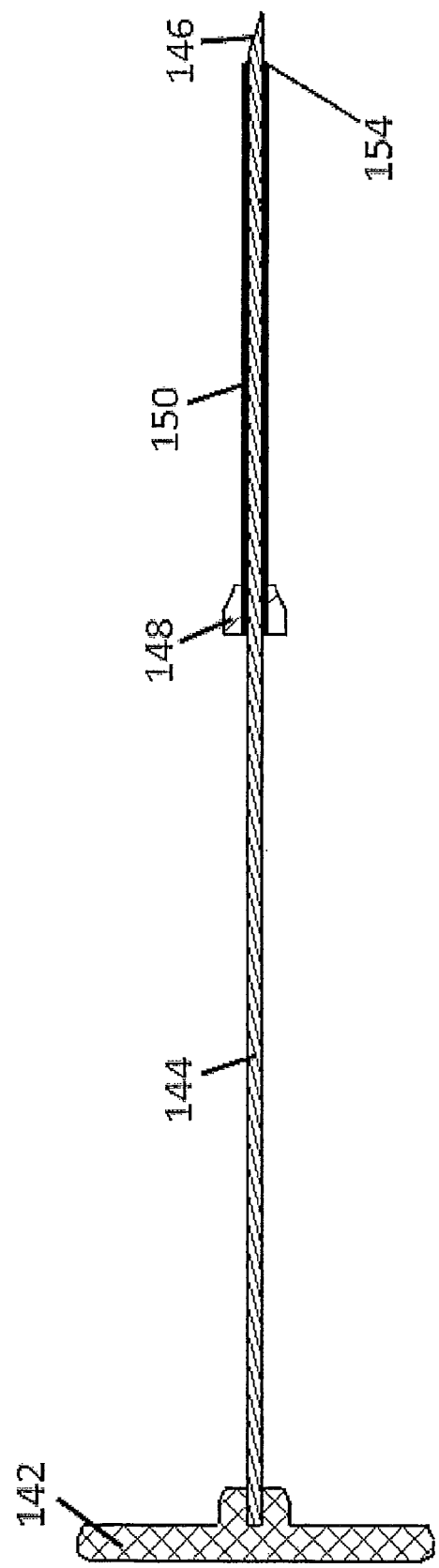
FIG. 10c is a cross section showing the relative positioning of the inner stylet of FIG. 10a within the outer penetrating member of FIG. 10b for use in a third embodiment of the present invention.
Figure 11:
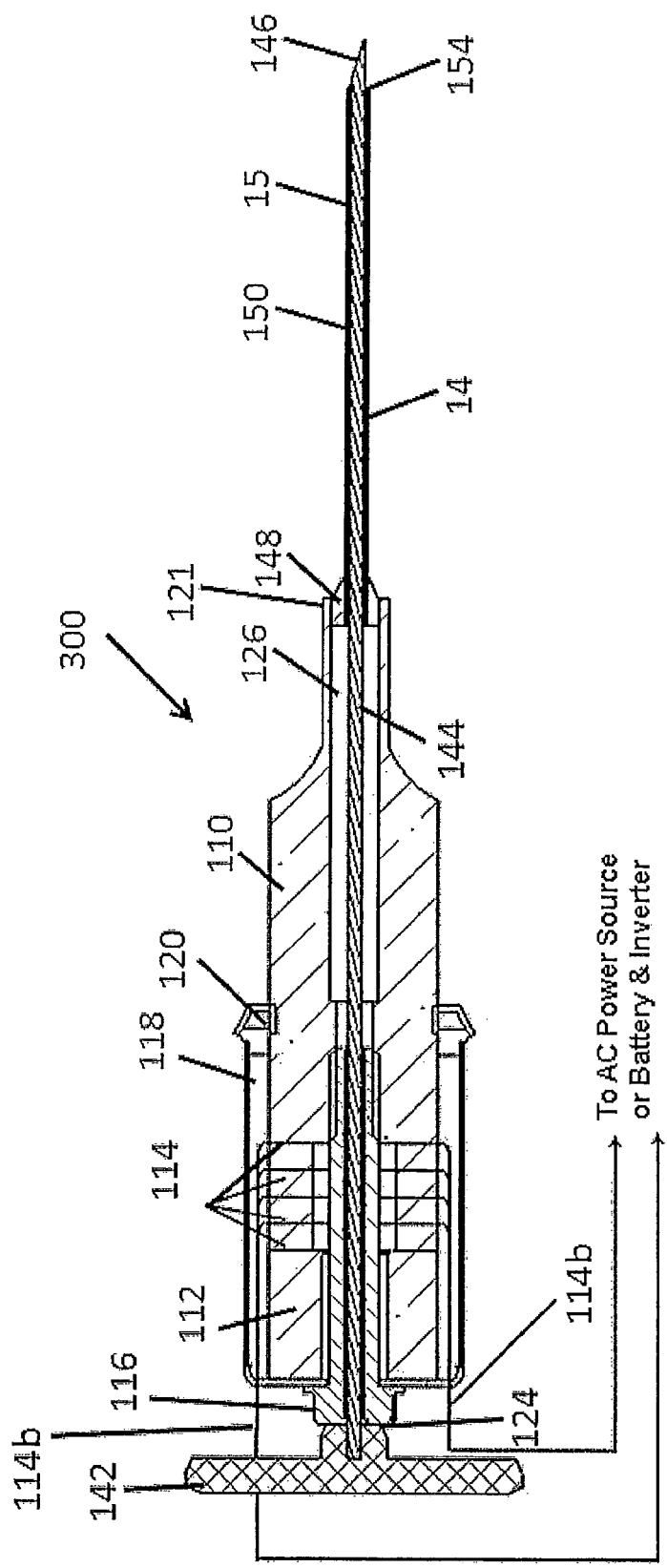
FIG. 11 is a cross section of a third embodiment of the present invention.

Referring now to FIG. 11, inner stylet 14 is slidably disposed within bore 126 of Langevin actuator 100 of FIG. 4 and outer trocar tube 15 of FIG. 10b, with outer trocar tube 15 attached to horn 110 to form a bone biopsy device, generally designated as 300. Inner stylet 14 extends in a manner such that handle 142 contacts bolt 116 when fully seated, with inner stylet shaft extending from handle 142 through proximal opening 124, through bore 126 and hollow portion of outer trocar body 150 finally terminating as inner stylet tip 146 at a location beyond distal trocar tip 154. In this embodiment, when the at least one of piezoelectric elements 114 of Langevin actuator 100 of FIG. 4 is electrically actuated via electrical conductors 114b at a predetermined frequency, motion in the form of compression and expansion of the rings is transferred to an anti-node location at the distal face 121 of horn 110. The motion is then transferred as actuation of outer trocar tube 15 of FIG. 10b.

Figure 12:
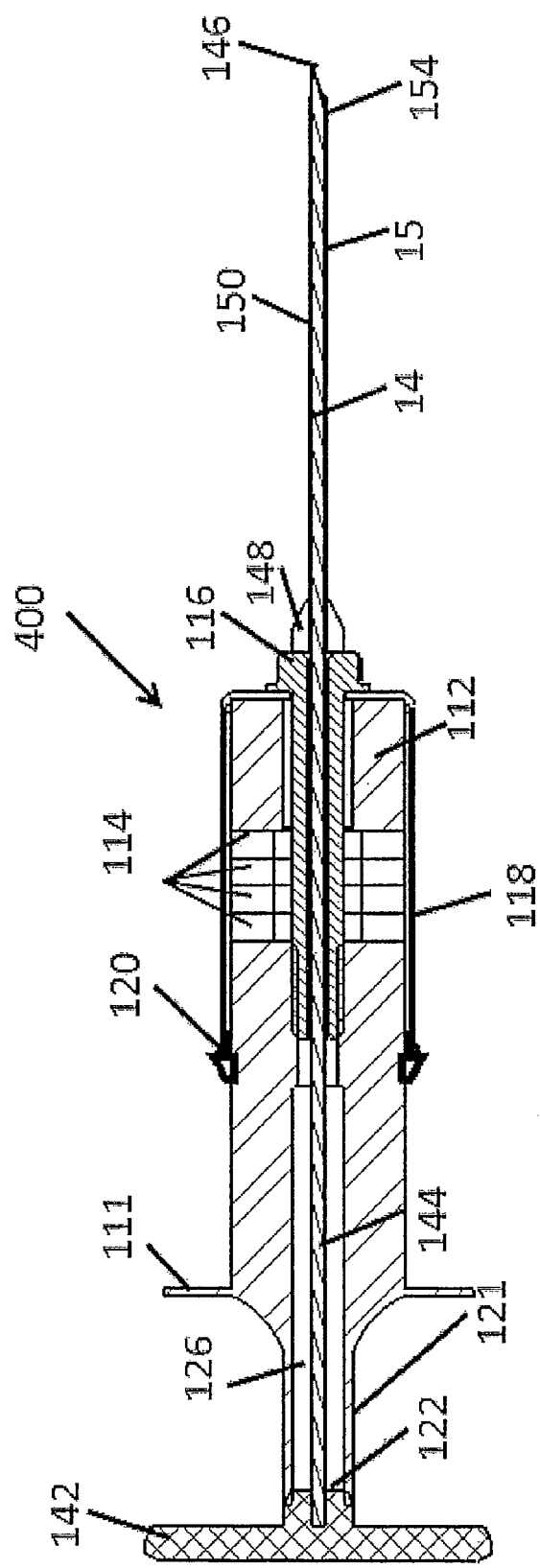
FIG. 12 is a cross section of a fourth embodiment of the present invention.

In an alternate embodiment, an advanced bone biopsy device, generally indicated as 400, shown in FIG. 12, comprises all of the elements of bone biopsy device 300 of FIG. 11, except that upon electrical activation of Langevin actuator 100 of FIG. 4 at a predetermined frequency, the motion is transferred as actuation of inner stylet 14. To perform this function, the positioning of the inner stylet shaft 14 of FIG. 10a and outer trocar tube 15 of FIG. 10b are inverted with respect to the configuration of FIG. 11. For example, in the advanced bone biopsy device 400, outer trocar tube 15 is attached to bolt 116. Additionally, inner stylet 14 extends in a manner such that handle 142 contacts distal face 121 of horn 110 when fully seated, with inner stylet shaft 144 extending from handle 142 through distal opening 122, through bore 126 and hollow portion of outer trocar body 150, finally terminating as inner stylet tip 146 at a location beyond distal trocar tip 154.

Figure 13:
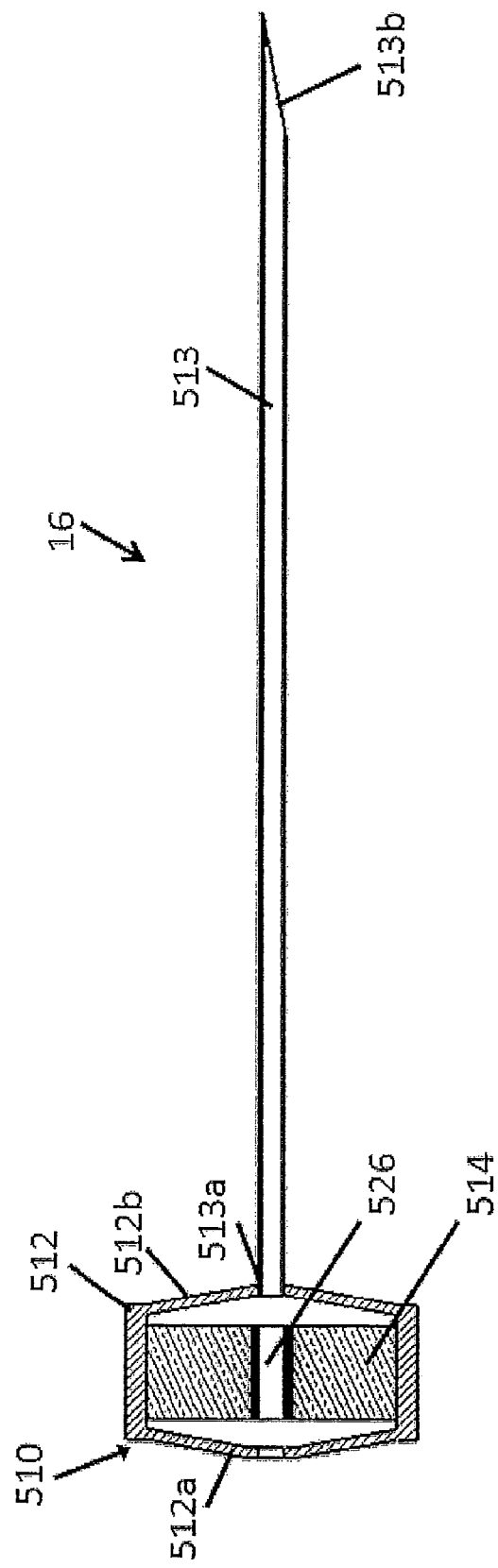
FIG. 13 is a cross section of a penetrating member attached to an amplified piezoelectric actuator for use in a fifth embodiment of the present invention.
Figure 13A:
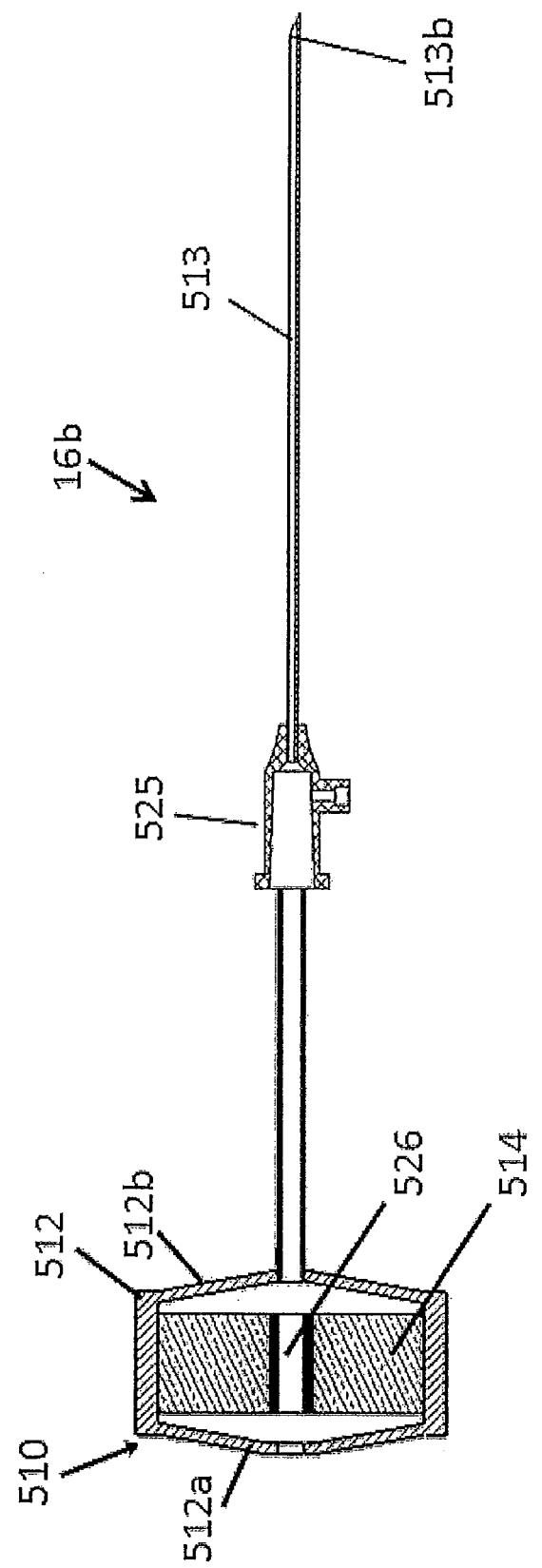
FIG. 13a is cross section of an alternate APA design of a penetrating member with side port for use the present invention.
Figure 14:
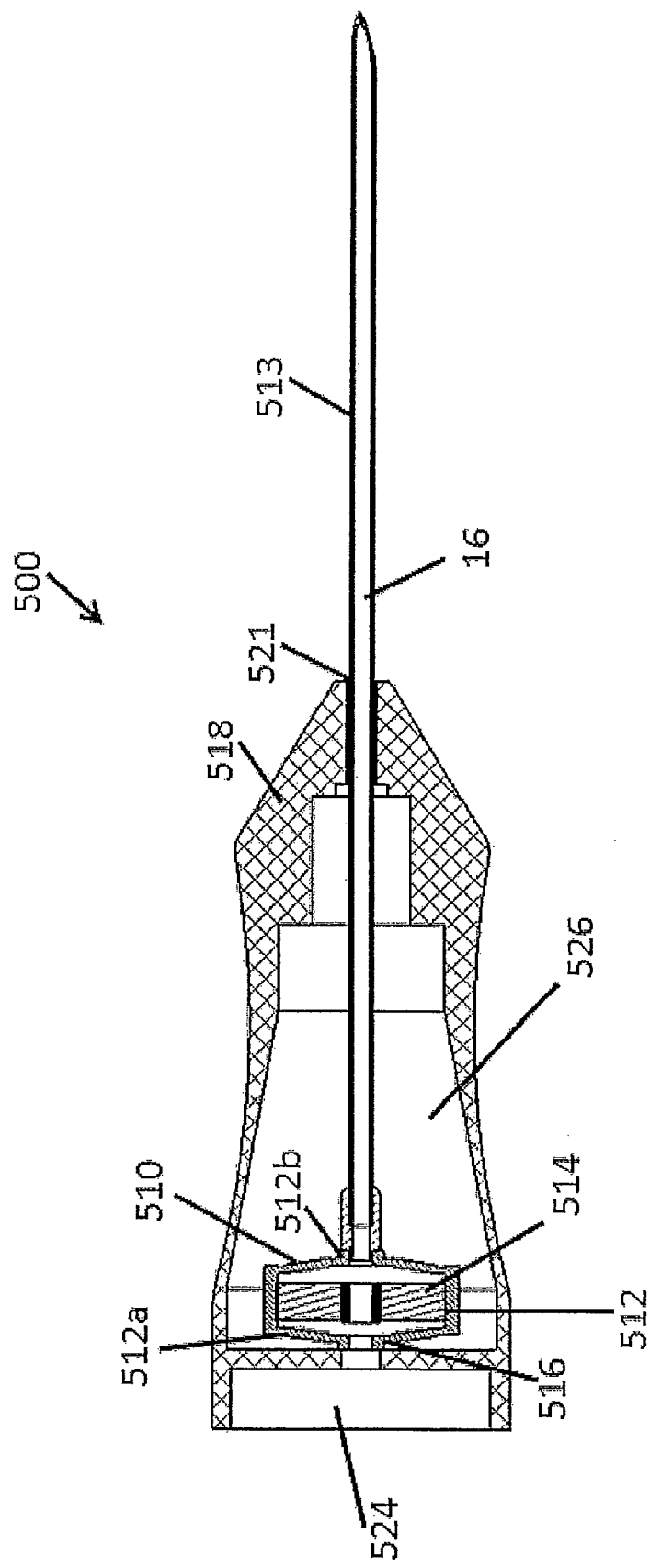
FIG. 14 is a cross section of a fifth embodiment of the present invention.
Figure 14A:
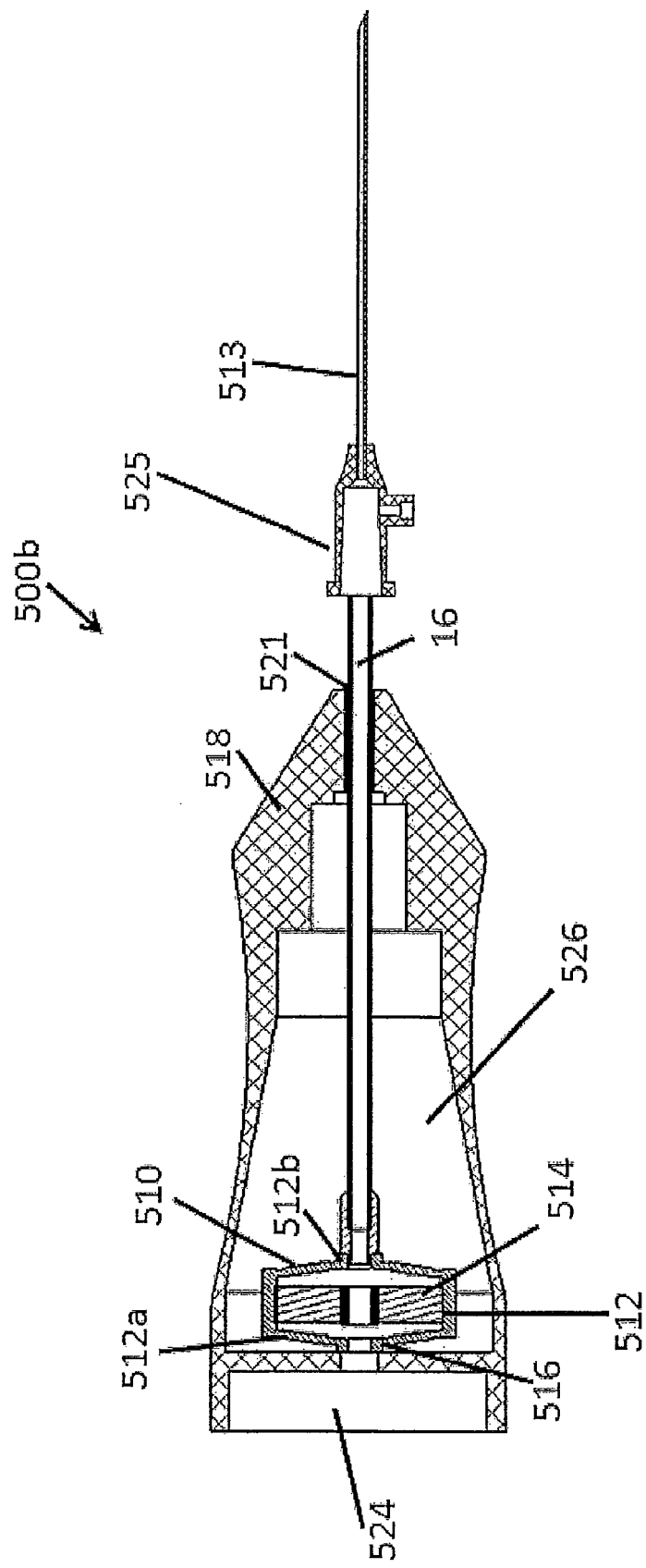

While the previous embodiments have been described with respect to a Langevin actuator 100 as the actuating mechanism, the invention is not so limited. For example, as shown in FIG. 13, a hollow tubular structure having a sharpened distal tip 513b of the penetrating member 513 is attached at its proximal end 513a to an Amplified piezoelectric actuator (APA) 510 forming an APA needle, generally designated as 16. The amplified piezoelectric actuator (APA) 510 comprises a frame 512, normally formed of a metal such as brass or stainless steel, and a piezoelectric material 514 compressed within frame 512. An APA bore 526 may extend from a distal face through piezoelectric material 514 and through a proximal face 512a of frame 512. Hollow penetrating member 513, for example a hypodermic needle, is attached to the distal face 512b of frame 512, such that the hollow portion is concentrically aligned with the APA bore 526. As shown in FIG. 14, APA needle 16 may be disposed within a handle 518 forming an APA syringe, generally designated as 500. Important to this embodiment is that a proximal face 512a of frame 512 of amplified piezoelectric actuator (APA) 510 must be fixed as shown at 516 attachment point to an inner portion of the handle 518 such that the APA bore 526, hollow penetrating member 513, a handle proximal opening 524 and handle distal opening 521 form a continuous channel through which fluids may pass into a patient. FIGS. 13a and 14a show alternate embodiments 16b and 500b, respectively, with a detachable penetrating member hub 525 enabling the single use penetrating member with re-usable active motion handle where the penetrating member hub 525 is described previously.

In operation, the piezoelectric material 514 expands during the AC voltage cycle, which causes the frame's proximal and distal faces 512a, 512b formed opposite of one another to move inward toward each other. Conversely, when piezoelectric material 514 compresses during the opposite AC cycle, an outward displacement of the frame's proximal and distal faces 512a, 512b away from one another occurs. However, in the present embodiment, the proximal face 512a of the frame is fixedly attached to body's 518 attachment point 516 so that any movement in the piezoelectric material stack will result in only a relative motion of distal face 512b and, thereby, a motion of the penetrating member 513.

Two examples of applicable amplified piezoelectric actuators (APAs) are the non-hinged type, and the grooved or hinged type. Details of the mechanics, operation and design of an example hinged or grooved APA are described in U.S. Pat. No. 6,465,936 (Knowles et al.), which is hereby incorporated by reference in its entirety. An example of a non-hinged APA is the Cedrat APA50XS, sold by Cedrat Technologies, and described in the Cedrat Piezo Products Catalogue "Piezo Actuators & Electronics" (Copyright® Cedrat Technologies June 2005).

Preferably, the APAs of the present invention are operated at frequencies in the range of 100 Hz to 20 kHz, more preferably 100 Hz to 1 kHz.

Figure 15:
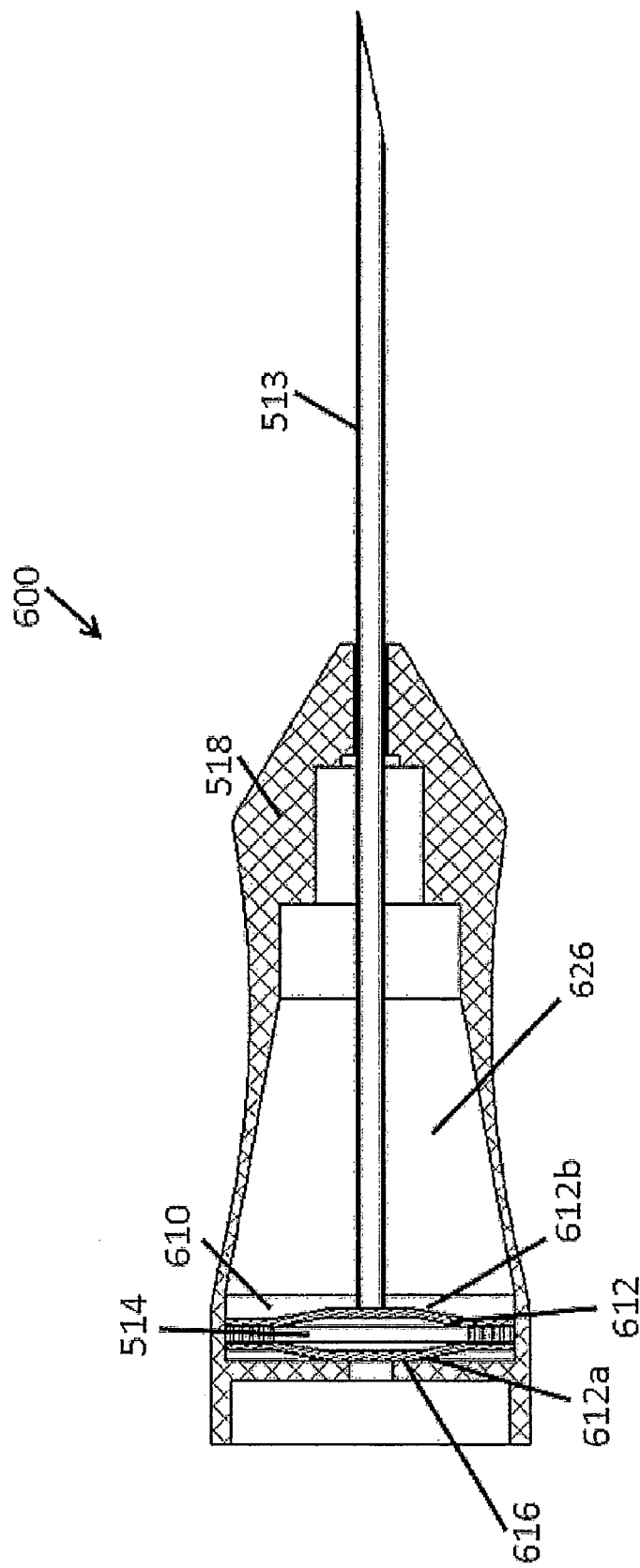
FIG. 15 is a cross section of a sixth embodiment of the present invention comprising a Cymbal actuator.

Alternatively, the actuator of the present invention may be a Cymbal actuator. For example, in FIG. 15, a Cymbal syringe, generally indicated as 600, including a Cymbal actuator 610 which comprises two endcaps 612 with the distal endcap 612b and proximal endcap 612a with at least a piezoelectric element 514 formed between the endcaps. The Cymbal syringe is centered on the Cymbal bore 626. The endcaps 612 enhance the mechanical response to an electrical input, or conversely, the electrical output generated by a mechanical load. Details of the flextensional Cymbal actuator technology is described by Meyer Jr., R. J., et al., "Displacement amplification of electroactive materials using the Cymbal flextensional transducer", Sensors and Actuators A 87 (2001), 157-162. By way of example, a Class V flextensional Cymbal actuator has a thickness of less than about 2 mm, weighs less than about 3 grams and resonates between about 1 and 100 kHz depending on geometry. With the low profile of the Cymbal design, high frequency radial motions of the piezoelectric material are transformed into low frequency (about 20-50 kHz) displacement motions through the cap-covered cavity. An example of a Cymbal actuator is described in U.S. Pat. No. 5,729,077 (Newnham et al.) and is hereby incorporated by reference. While the endcaps shown in the figures are round, they are not intended to be limited to only one shape or design. For example, a rectangular Cymbal endcap design is disclosed in Smith N. B., et al., "Rectangular Cymbal arrays for improved ultrasonic transdermal insulin delivery", J. Acoust. Soc. Am. Vol. 122, issue 4, October 2007. Cymbal actuators take advantage of the combined expansion in the piezoelectric charge coefficient $d_{33}$ (induced strain in direction 3 per unit field applied in direction 3) and contraction in the $d_{31}$ (induced strain in direction 1 per unit field applied in direction 3) of a piezoelectric material, along with the flextensional displacement of the endcaps 612, which is illustrated in FIG. 15. The design of the endcaps 612 allows both the longitudinal and transverse responses to contribute to the strain in the desired direction, creating an effective piezoelectric charge constant ($d_{eff}$) according to the formula, $d_{eff} = d_{33} + (-A*d_{31})$. Since $d_{31}$ is negative, and the amplification factor (A) can be as high as 100 as the endcaps 612 bend, the increase in displacement generated by the Cymbal compared to the piezoelectric material alone is significant. The endcaps 612 can be made of a variety of materials, such as brass, steel, titanium or KOVAR™, a nickel-cobalt ferrous alloy compatible with the thermal expansion of borosilicate glass which allows direct mechanical connections over a range of temperatures, optimized for performance and application conditions. The endcaps 612 also provide additional mechanical stability, ensuring long lifetimes for the Cymbal actuators.

Figure 16:
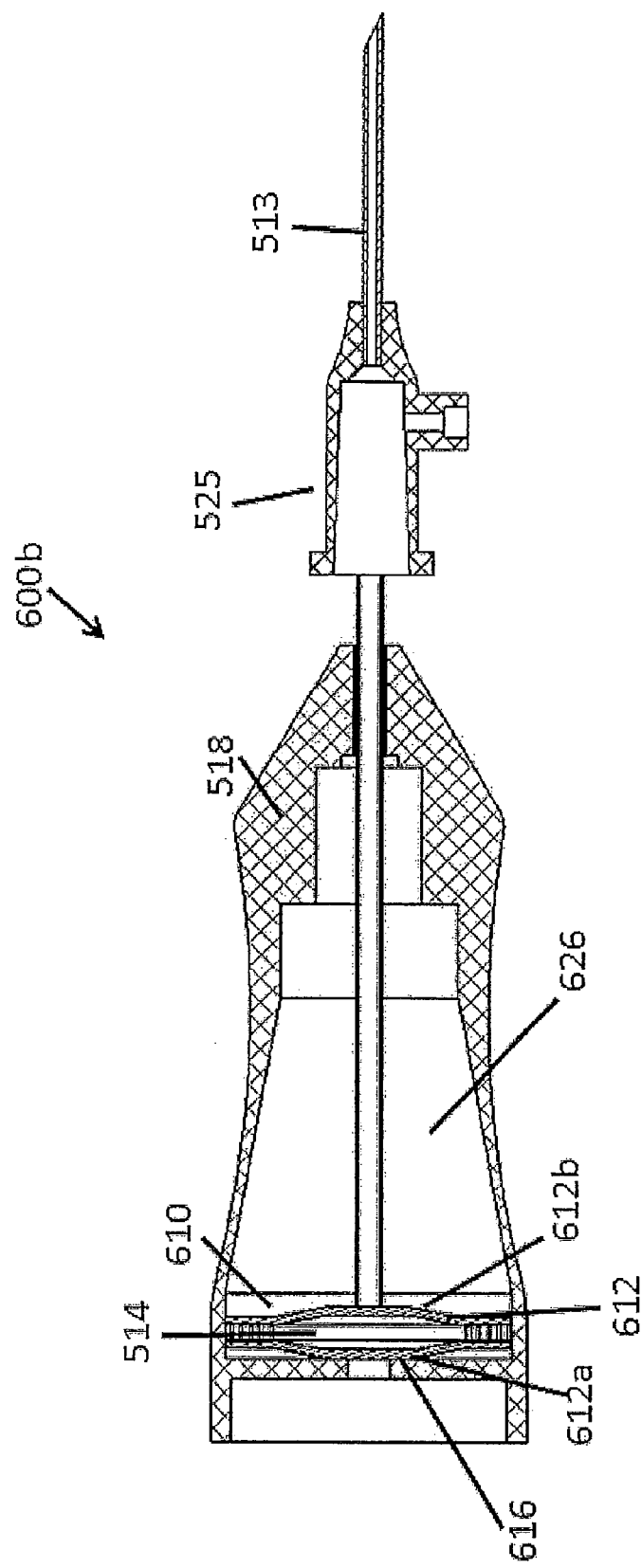

The Cymbal actuator 610 drives the penetrating member 513. When activated by an AC current, the Cymbal actuator 610 vibrates sinusoidally with respect to the current's frequency. Because endcap 612a is fixed to an inner sidewall of body 518, when Cymbal actuator 610 is activated, endcap 612b moves with respect to the body in a direction parallel to the hypothetical long axis of the medical device. Further, the displacement of penetrating member 513 is amplified relative to the displacement originating at piezoelectric material 514 when it compresses and expands during activation due in part to the amplification caused by the design of endcaps 612. For example, the piezoelectric material 514 alone may only displace by about 1-2 microns, but attached to the endcaps 612, the Cymbal actuator 610 as a whole may generate up to about 1 kN (225 lb-f) of force and about 80 to 100 microns of displacement. This motion is further transferred through the penetrating member 513 as an amplified longitudinal displacement of 100-300 microns. For cases requiring higher displacement, a plurality of Cymbal actuators 610 can be stacked endcap-to-endcap to increase the total longitudinal displacement of the penetrating member 513. FIG. 16 shows an alternate embodiment 600b with a detachable penetrating member hub 525 enabling the single use penetrating member with reusable active motion handle.

In alternate embodiments of the present invention, an additional port opening is formed in communication with a channel formed within the body of the actuator, for example a Langevin actuator. In particular, FIGS. 17-19 are directed to these alternate embodiments and it should be noted that for clarity reasons, the handle 118 of the Langevin actuator is not shown in these figures.

Because the port opening is provided so as to attach a means for providing visual, audible or tactile feedback response (e.g., using any well-known detection mechanisms such as but not limited to electrical, magnetic, pressure, capacitive, inductive, etc. means) to indicate the successful penetration of the specific tissue such as the epidural space, it must be formed at a location which will be least detrimental to such means. In other words, because the actuator vibrates at high frequencies, each point along the actuator experiences a different displacement defined by a standing wave. In FIG. 17, a displacement graph G1 represents a standing wave having longitudinal displacements at points along the length of a Langevin actuator operated at 38 kHz. As can be seen in a displacement graph G1, two nodes having near zero displacement exist at particular locations in the standing wave. The two node ("zero node" ZN) locations on the Langevin actuator LT are therefore defined at a particular lengths along the Langevin actuator. In the specific design shown in FIG. 17 the nodes on the standing wave correspond to zero node, or locations having minimum displacements on the Langevin actuator LT. The locations of the zero nodes on the Langevin actuator LT are then located at a proximal face (not shown) of the rear mass opposite to the distal face 121. Line ZN defines the physical location of the other zero node at which a side port SP should be located, preferably centered, when formed in a Langevin actuator LT relative to second zero node of the standing wave in displacement graph G1. In the case shown in FIG. 17, the side port SP is formed at the horn 110 of the Langevin actuator LT, however a port opening is not necessarily so limited. A port opening can be placed anywhere along an actuator but a zero node location is preferred.

Figure 17A:
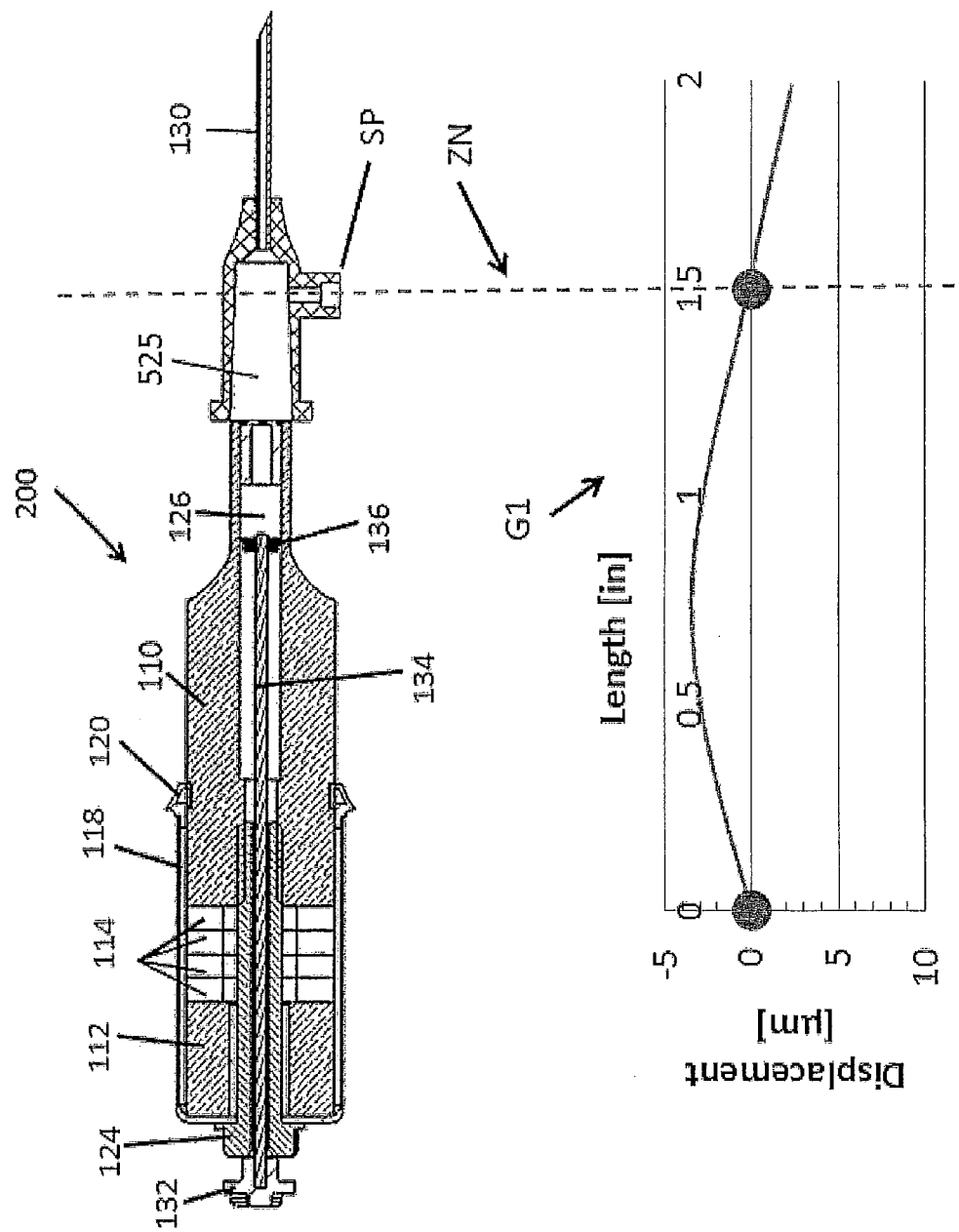
FIG. 17a shows the correlation between zero node points of a standing wave and the location of a side port on the penetrating member connected to the Langevin actuator.

In a more preferred embodiment, FIG. 17a describes the side port SP location on the zero node ZN of the penetrating member hub 525. In this embodiment, the design length includes both the needle length and actuator length to achieve the zero node ZN on the hollow needle 130 which includes length of penetrating member hub 525. A side port SP can be placed anywhere along hollow needle 130 but a zero node location on the penetrating member hub 525 is preferred.

Figure 18A:
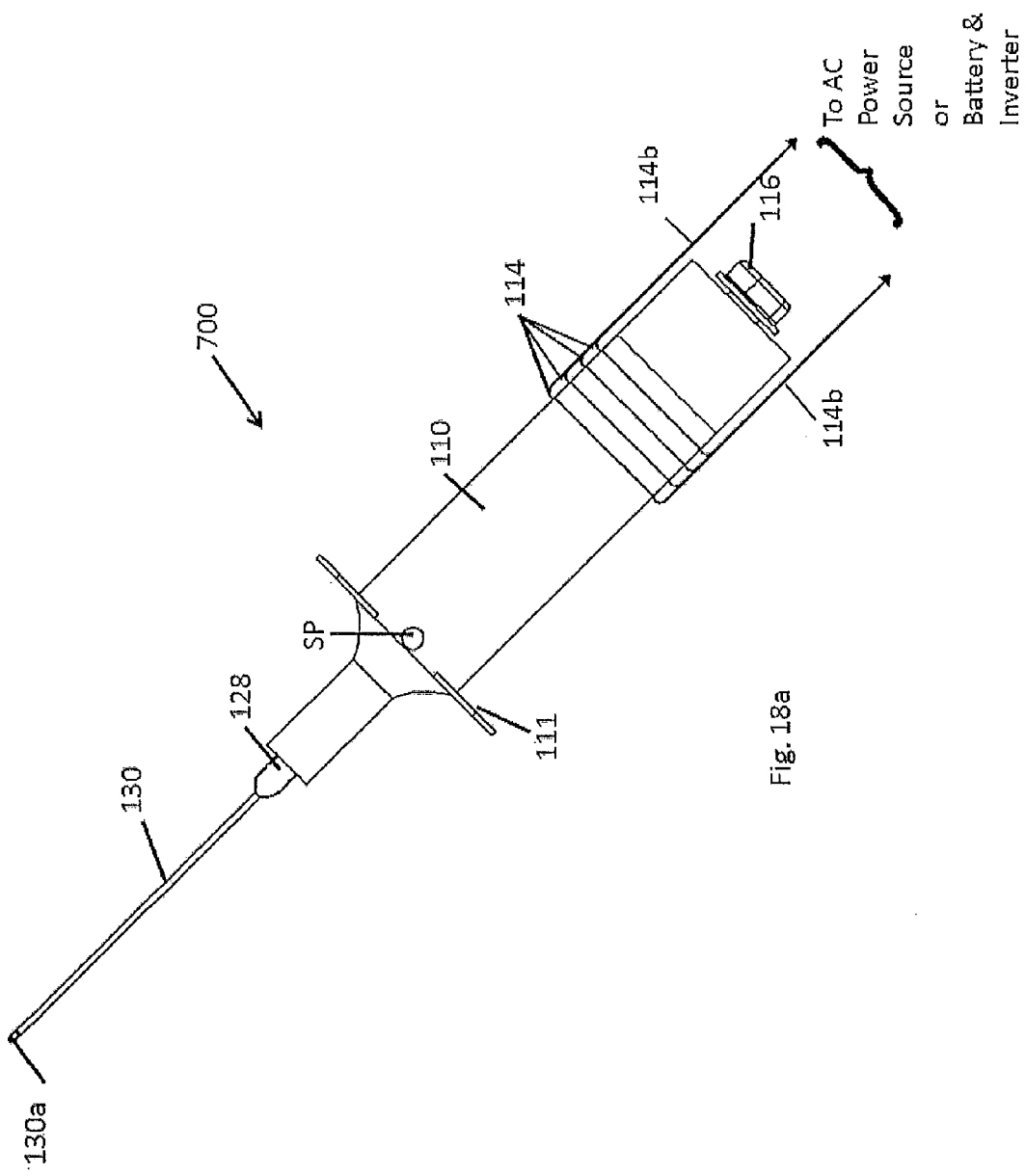
FIG. 18a is a functional diagram of a seventh embodiment of the present invention depicting a side port at a zero node location on a Langevin actuator without the handle shown.
Figure 19:
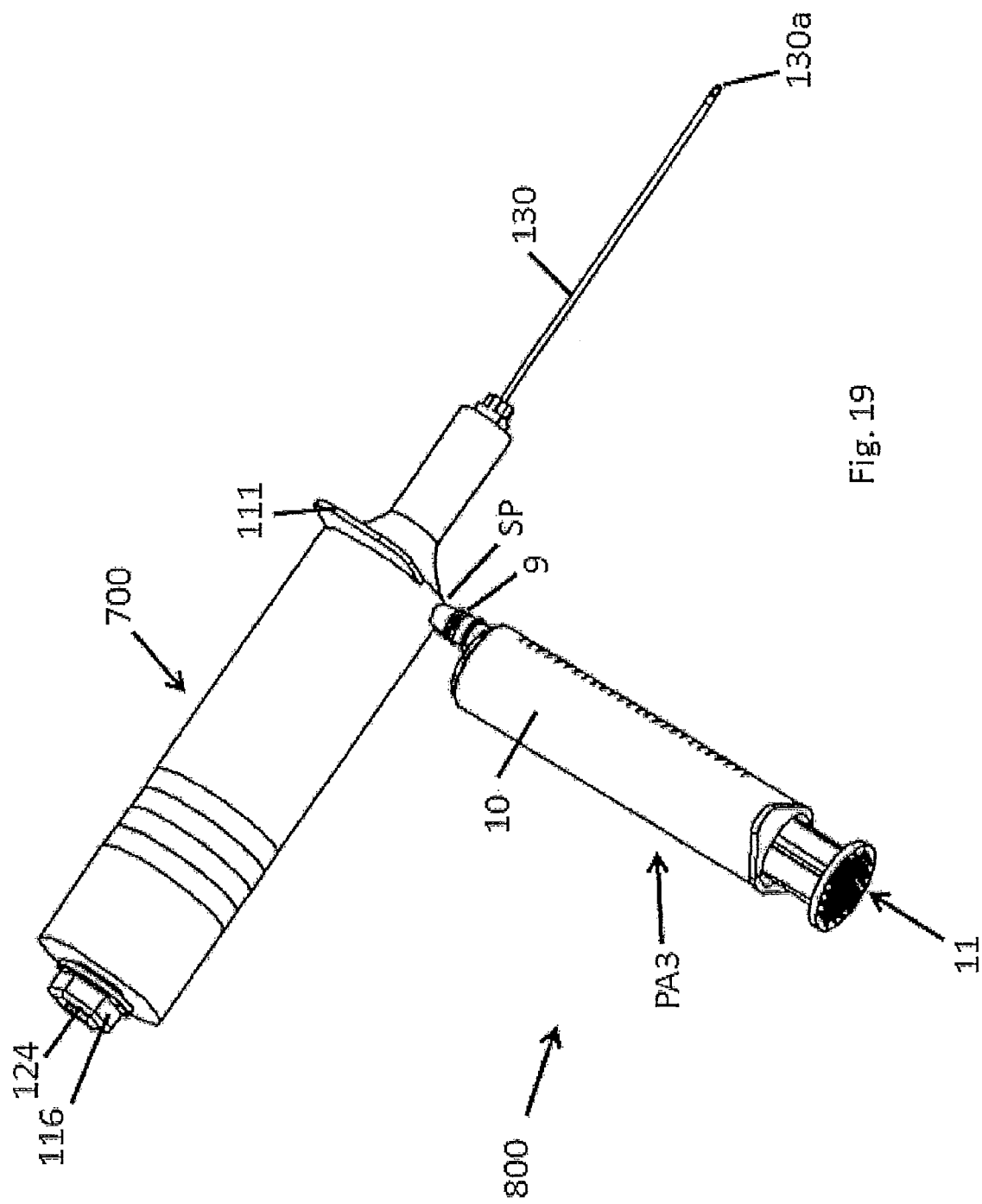
FIG. 19 is a drawing of a ninth embodiment of the present invention comprising a conventional syringe of FIG. 2a attached at the side port location of the actuator shown in FIG. 18 and without the actuator handle shown.

In FIG. 18a, a general side port configuration 700 of the present invention is shown with a side port SP as the port opening centered at a zero node location along the horn 110. Support wings 111 are also formed at a zero node to assist the clinician is holding and stabilizing the device.

Figure 18B:
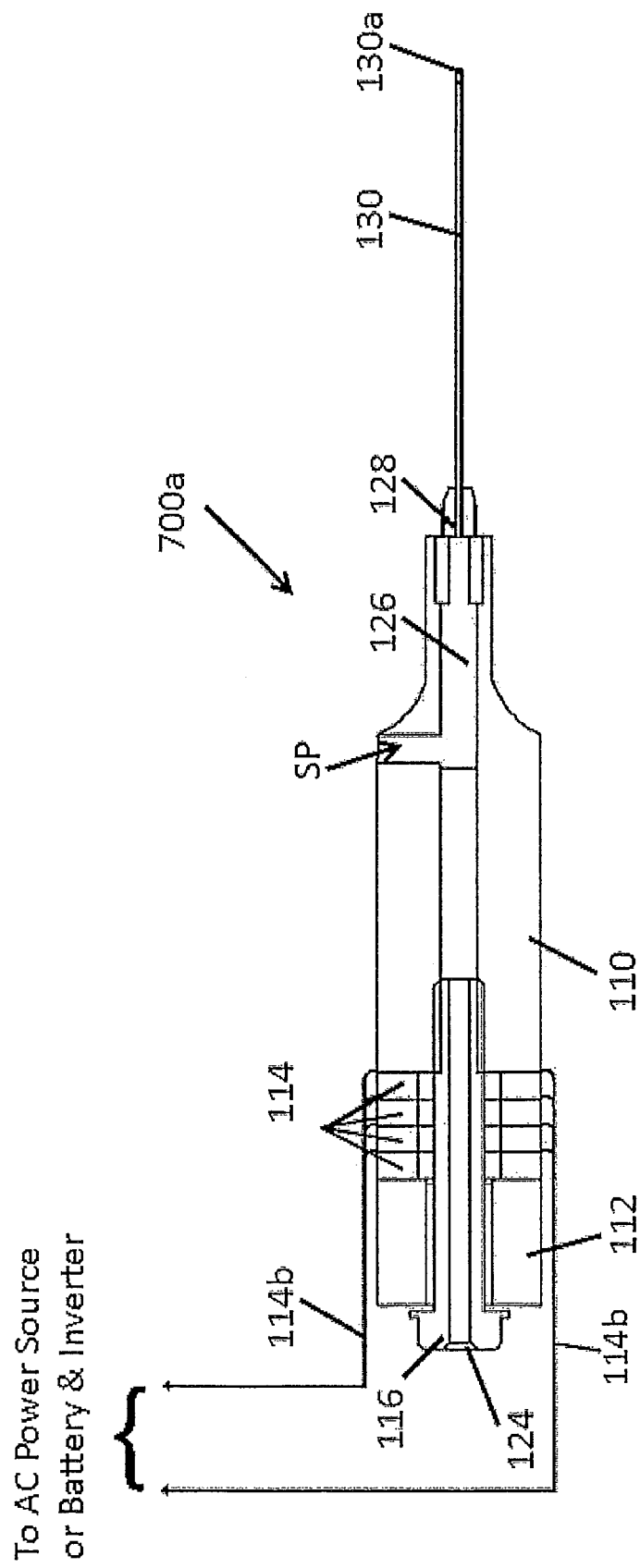
FIG. 18b is a functional diagram of a seventh embodiment of the present invention comprising the side port of FIG. 18a in communication with a central channel extending the length of a Langevin actuator and without the handle shown.

In a seventh embodiment of the present invention shown in FIG. 18b, a first side port configuration 700a has a channel for passing liquid, air or other materials comprises a continuous path from the proximal opening 124 through bore 126 passing through a distal opening (not shown) and extending through hollow needle 130 ending at a distal end 130a of the hollow needle which is open. In this seventh embodiment, the channel is in communication with the side port SP at a location along bore 126. Preferably, the side port SP is located at such a location along the actuator forming the first side port configuration 700a that acts as a zero node upon activating the device to vibrate.

Figure 18C:
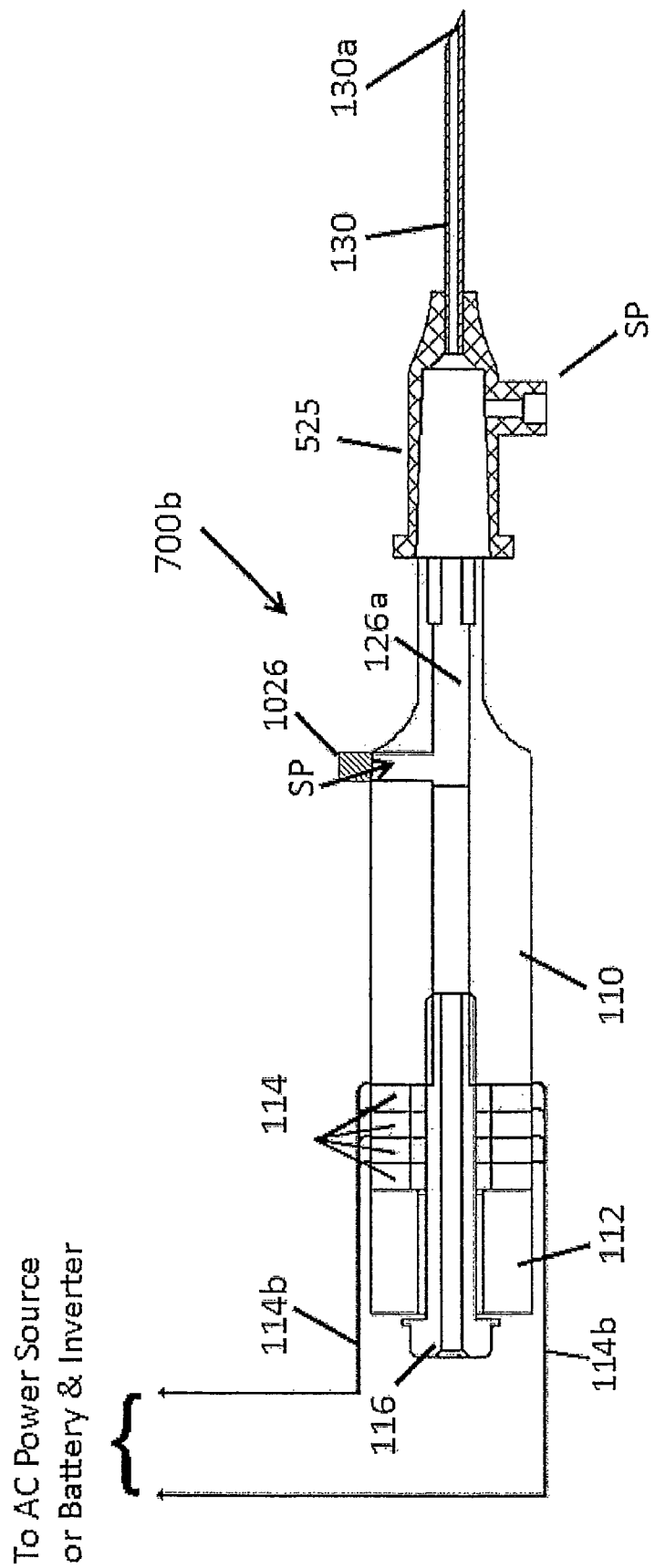
FIG. 18c is a sketch of a eighth embodiment of the present invention comprising two side ports in communication with needle attachment one connected to the front portion of the Langevin actuator and the other connected to the penetrating member without the actuator handle shown.

Alternatively, as shown in an eighth embodiment of the invention in FIG. 18c, a second side port configuration 700b has a channel for passing liquid, air or other materials comprises a continuous path located on the hollow needle 130 penetrating member hub 525. In this eighth embodiment, the channel is in communication with the side port SP at a location along penetrating member hub 525. Preferably, the side port SP is located at such a location along the entire length (actuator and penetrating member) forming the second side port configuration 700b that acts as a zero node upon activating the device to vibrate. In a secondary side port SP located on the actuator an indicator such as a light emitting diode 1026 can be attached and connected to the electronics to indicate a visual loss of resistance.

Figure 18D:
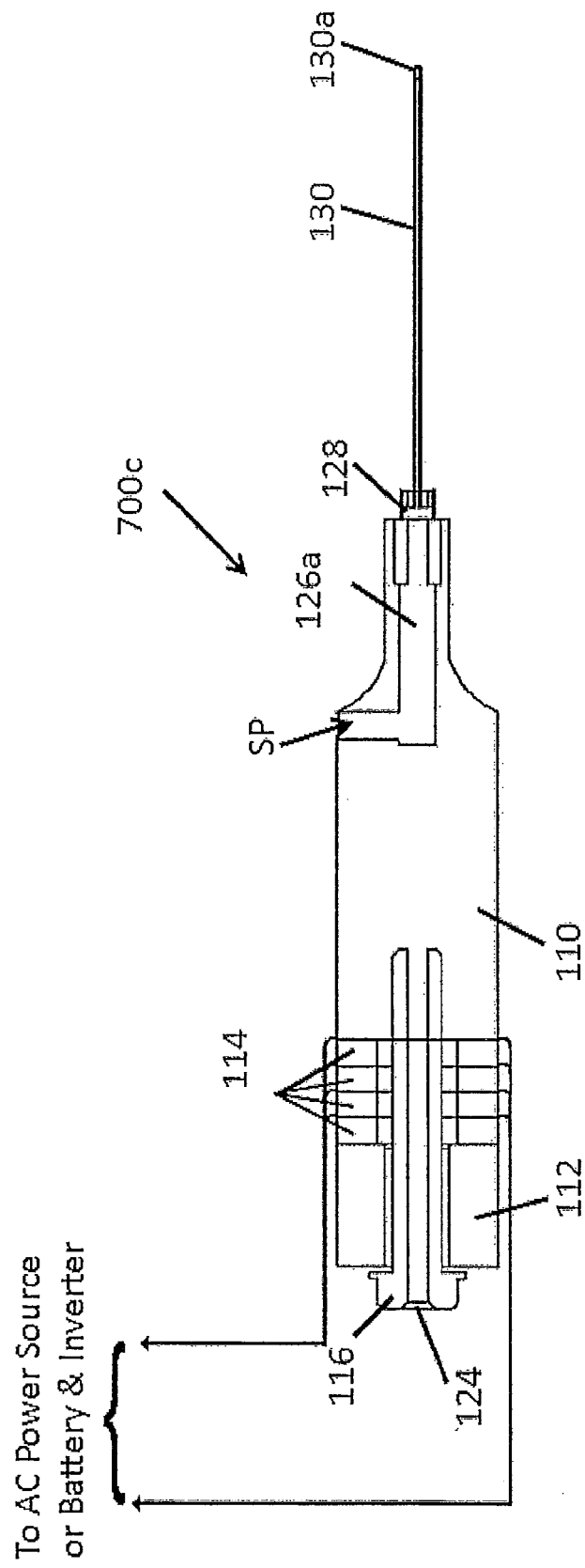

Alternatively, as shown in an eighth embodiment of the invention in FIG. 18d, a second side port SP configuration 700c has a small bore 126a for passing liquid, air or other materials located at zero node ZN to and from the hollow needle 130.

In a ninth embodiment of the present invention shown in FIG. 19, a feedback capable reduction of force tool 800 is provided. By way of example only, tool 800 comprises a means for providing tactile feedback response via a conventional loss of resistance syringe PA3 having a biasing element 11 with a plunger or balloon (e.g., elastomer device) or any other device that creates pressure then detects or measures pressure change. This device is coupled at a port location, preferably a side port SP located, via, by way of example only, a Luer Taper, male/female connector, screw-type connector, and preferably centered, at a zero node location. The tool 800 also includes an indicator in communication with the actuator 700 such as, but not limited to, an audible indicator, tactile indicator, or visual (e.g., deflation, optical, etc.).

Figure 19A:
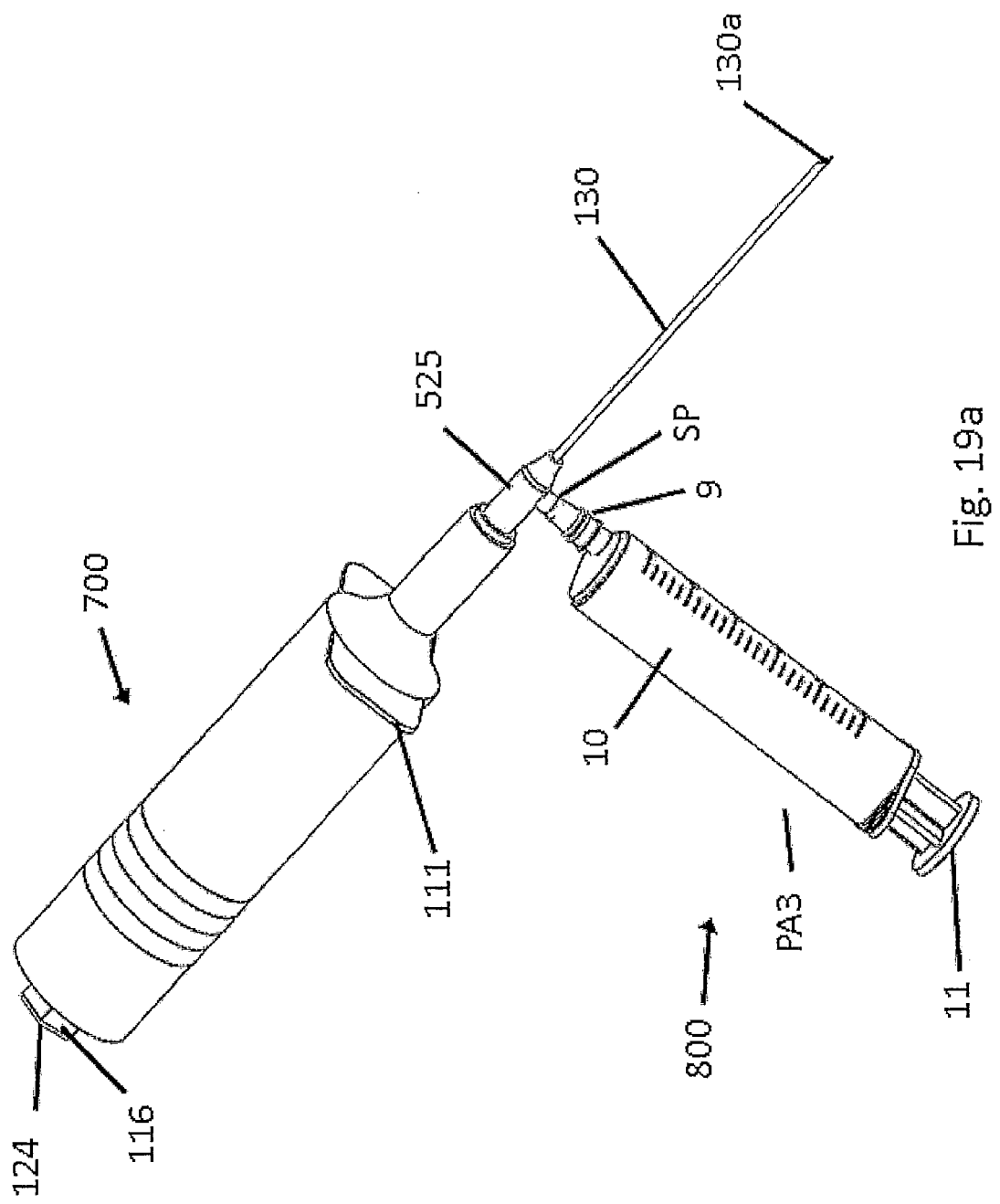
FIG. 19a is a drawing of a ninth embodiment of the present invention comprising a conventional syringe of FIG. 2a attached at the side port location of the penetrating member hub shown in FIG. 18c with the actuator also connected into the hub and without the actuator handle shown.

In a most preferred embodiment of the present invention shown in FIG. 19a, a feedback capable reduction of force tool 800 is located on the hollow needle 130 at a zero node ZN on the penetrating member hub 525.

Figure 19B:
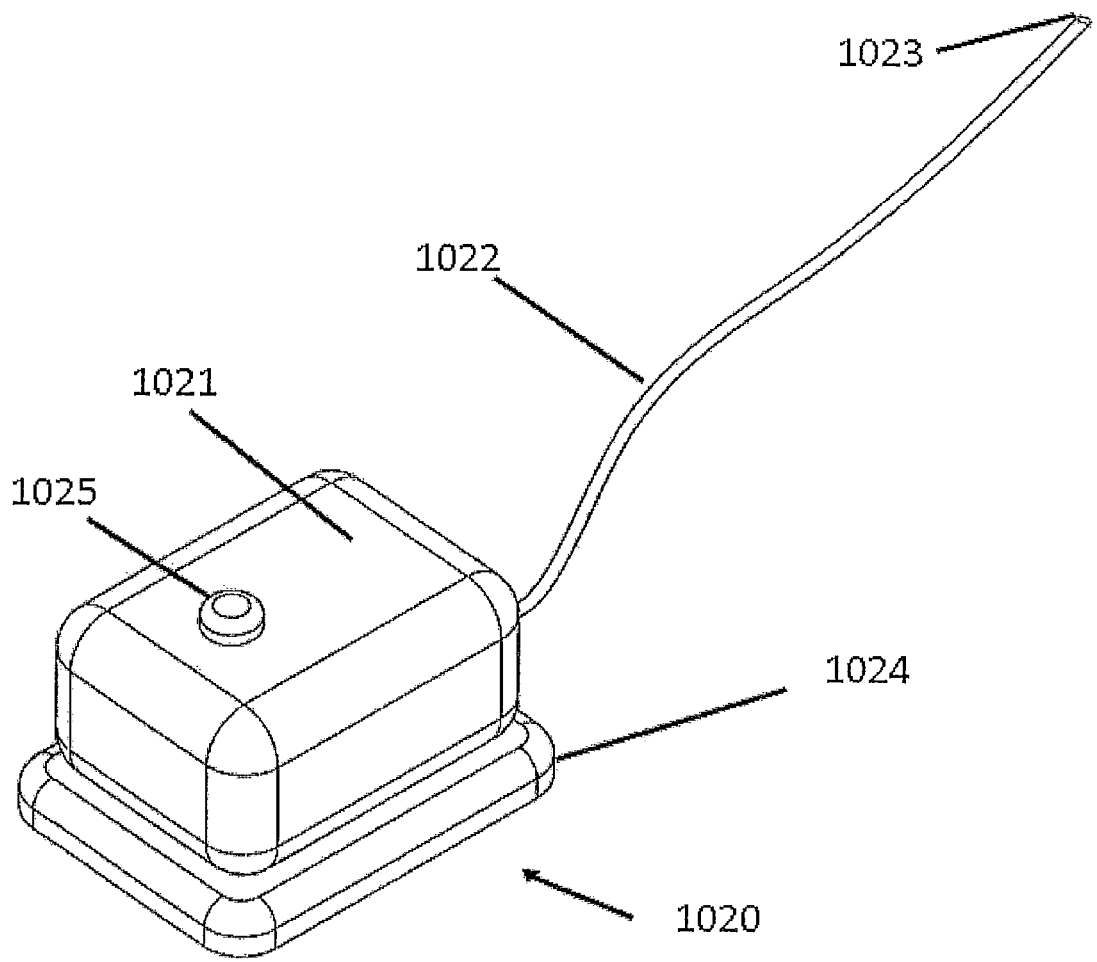
FIG. 19b is a drawing of a pressure sensing pump system for connection to a penetrating member.

Another embodiment described in FIG. 19b, a possible pressure sensor feedback system 1020 containing a small pumping mechanism equipped with a pressure or flow sensor to meter the amount of fluid being moved, a reservoir 1021 mounted on a base 1024. The pump fills with saline and connect via flexible tubing 1022 via an attachment fitting 1023 to the side port SP of the penetrating member. When loss of resistance (LOR) is detected, the electronic control system will close a switch and an indicator such as a light emitting diode (LED) (not shown) located on the side port SP of the actuator will turn-on indicating loss of resistance. The electronics control system at this point will turn the actuator off so that forward motion ceases. In additional embodiment, besides the visual signal, an audible signal a 'beep' could be incorporated into the pump system.

By way of example only, the following is an exemplary method of using the present invention, whereby a clinician uses the present invention for an epidural procedure. When performing an epidural procedure, the clinician first fills syringe PA3 with a fluid, such as a saline solution or air. The clinician then inserts the front portion 9 of the syringe into the side port SP of the actuator 700b. Upon electrically activating the actuator, the clinician holds actuator 700b with a first hand while pressing the distal end 130a of the hollow needle against a patient's back. The clinician continues to provide forward momentum, while also providing a biasing force against biasing element 11, advancing hollow needle 130. With continued forward momentum, the hollow needle punctures the supraspinous ligament, the instraspinous ligament, and the ligamentum flavum (see FIG. 7, for example). Upon puncturing the ligamentum flavum, the distal end 130a of the needle enters the epidural space at which point there is a pressure drop from the biasing element 11 to the opening at the distal end 130a. The pressure drop allows for the solution to be ejected from the opening at the distal end 130a, and the continued biasing of the biasing element 11 combined with the loss of volume of saline results in a loss of resistance (LOR) against the clinician's thumb and a visibly identifiable motion of the biasing element 11. When the biasing element moves due to this lack of resistance, the clinician quickly identifies that the epidural space has been successfully reached and quickly stops forward momentum of the actuator. Additionally, because the activation of the actuator results in a vibration of the needle 130, the clinician does not need to provide such a high penetration force and can quickly react to stop himself/herself before advancing the needle beyond the epidural space.

It should be further noted that it is within the broadest scope of the present invention to include syringes or other mechanisms which provide automatic biasing, such that the clinician does not have to apply a biasing force against the biasing element 11 prior to entry into, for example, the epidural space. In particular, the automatic biasing force (implemented, for example, via a spring, an elastomer, or any other well-known biasing mechanism such as, but not limited to, those described in U.S. Patent Publication No. 2007/0142766 (Sundar, et al.)) maintains an equal resistance as the needle is moved through the supraspinous ligament, the instraspinous ligament, and the ligamentum flavum. Upon entry into the epidural space, the biasing force is no longer resisted and this can be manifested in a variety of ways to the clinician, but not limited to, movement of the biasing element, or any other visual, audible or tactile indication using any well-known detection mechanisms such as but not limited to electrical, magnetic, pressure, capacitive, inductive, etc. means. For example, a pressure signal indicative of a loss of solution resistance automatically cuts off power to the driver actuator (e.g., piezoelectric elements, voice coil, solenoid, etc.).

While feedback means have been coupled to the side port SP, the invention is not so limited to feedback means. Any device may be coupled to a port location of the actuator, or ideally at the side port SP location even those devices simply being a means for providing or removing liquid, gas or other material such as a conventional syringe.

While the above-described embodiments of the present invention are made with respect to a handheld medical tool having a vibrating penetrating member and utilizing a Langevin actuator, Cymbal actuator, or APA for actuation, as mentioned earlier, the present invention is not limited to these actuator assemblies. Generally, any type of motor comprising an actuator assembly, further comprising a mass coupled to a piezoelectric material, or a voice coil motor, or solenoid, or any other translational motion device, would also fall within the spirit and scope of the invention. Furthermore, where the actuator assembly comprises a mass coupled to a piezoelectric material, the actuator assembly having a geometry which, upon actuation, amplifies the motion in a direction beyond the maximum strain of the piezoelectric material, would also fall within the spirit and scope of the present invention.

Figure 20A:
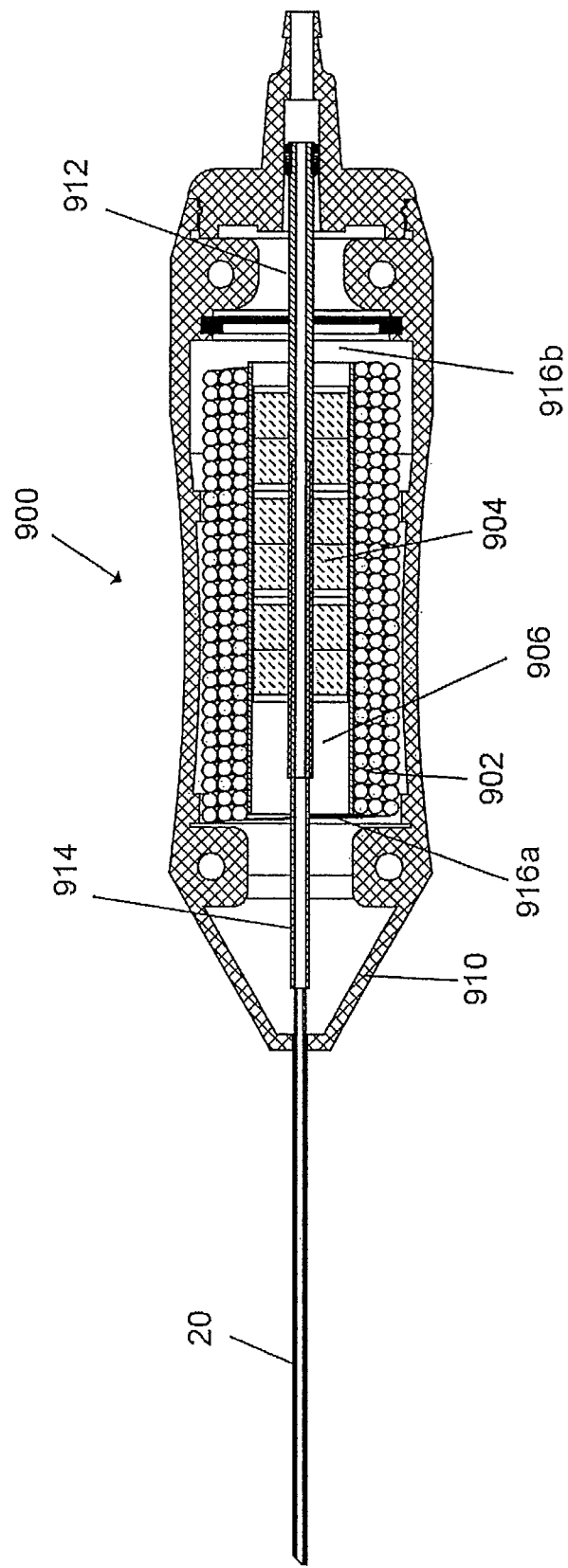
FIG. 20a is a cross-sectional view of a tenth embodiment of the present invention using a voice coil for the driving actuator.

FIG. 20*a* depicts an alternative embodiment 900 of the present invention using a voice coil for the driving actuator rather than piezoelectric elements. Voice coil actuator (also referred to as a "voice coil motor") creates low frequency reciprocating motion. The voice coil has a bandwidth of approximately 10-60 Hz and a displacement of up to 10 mm that is dependent upon applied AC voltage. In particular, when an alternating electric current is applied through the conducting coil 902, the result is a Lorentz Force in a direction defined by a function of the cross-product between the direction of current through the conductive coil 902 and magnetic field vectors of the magnetic member 904. The force results in a reciprocating motion of the magnetic member 904 relative to the coil support tube 906 which is held in place by the body 910. With the magnetic member 904 fixed to a driving tube 912, the driving tube 912 communicates this motion to an extension member 914 which in turn communicates motion to the penetrating member 20.

A first attachment point 916*a* fixes the distal end of the coil support tube 906 to the body 910. A second attachment point 916*b* fixes the proximal end of the coil support tube 906 to the body 910. The conducting coil may be made of different configurations including but not limited to several layers formed by a single wire, several layers formed of different wires either round or other geometric shapes. In a first embodiment of the conducting coil shown in FIG. 20*a*, a first layer of conductive wire is formed by wrapping the wire in a turn-like and spiral fashion and in a radial direction around the coil-support tube with each complete revolution forming a turn next to the previous one and down a first longitudinal direction of the coil support tube. After a predetermined number of turns, an additional layer is formed over the first layer by overlapping a first turn of a second layer of the wire over the last turn of the first layer and, while continuing to wrap the wire in the same radial direction as the first layer, forming a second spiral of wiring with at least the same number of turns as the first layer, each turn formed next to the previous one and in a longitudinal direction opposite to that of the direction in which the first layer was formed. In this embodiment, additional layers may be added by overlapping a first turn of each additional layer of the wire over the last turn of a previous layer and, while continuing to wrap the wire in the same radial direction as the previous layer, forming an additional spiral of wiring with at least the same number of turns as the previous layer, each turn formed next to the previous one and in a longitudinal direction opposite to that of the direction in which the previous layer is formed.

Figure 20B:
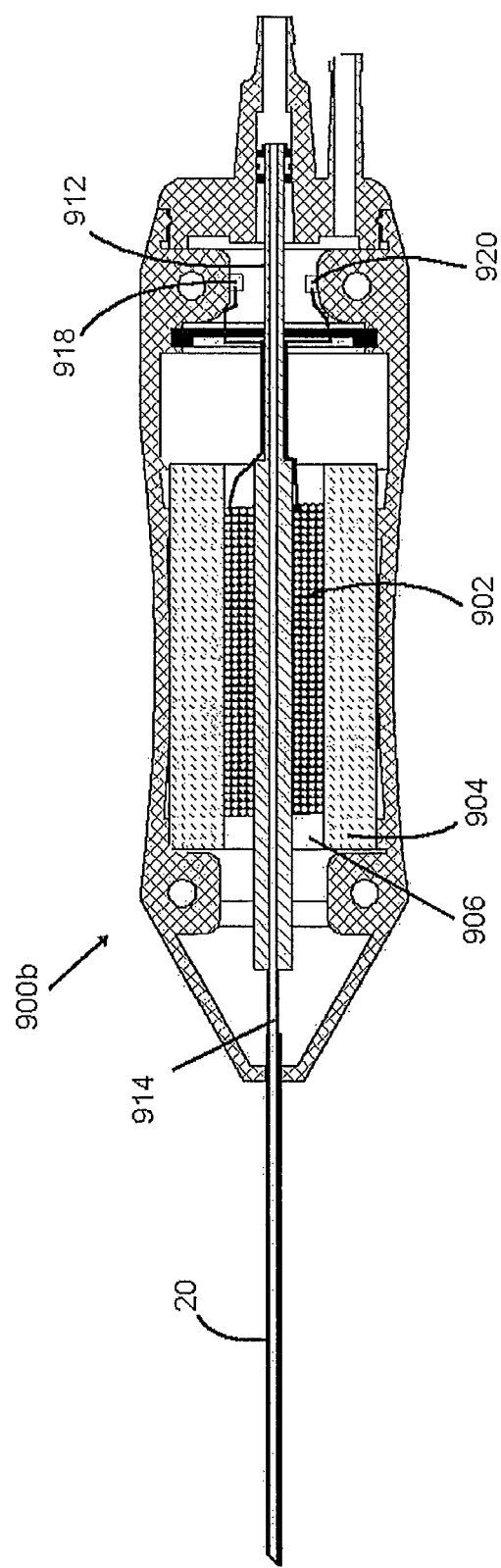

An alternative voice coil embodiment 900*b* is shown in FIG. 20*b*. In particular, in this alternative, the locations of the magnetic member 904 and conductive coil 902 are switched. In other words, the conductive coil is wrapped around and attached to the driving tube 912 and the magnetic member 904 is located along an outside radius of the coil support tube 906.

An electrical signal is applied at the conductive attachment sites 918 and 920 and causes the formation of the Lorentz force to form in an alternating direction that moves the conductive coil 902 and extension member 914 reciprocally along the longitudinal axis of the device. The conductive coils are physically in contact with the driving tube in this embodiment.

Figure 20C:
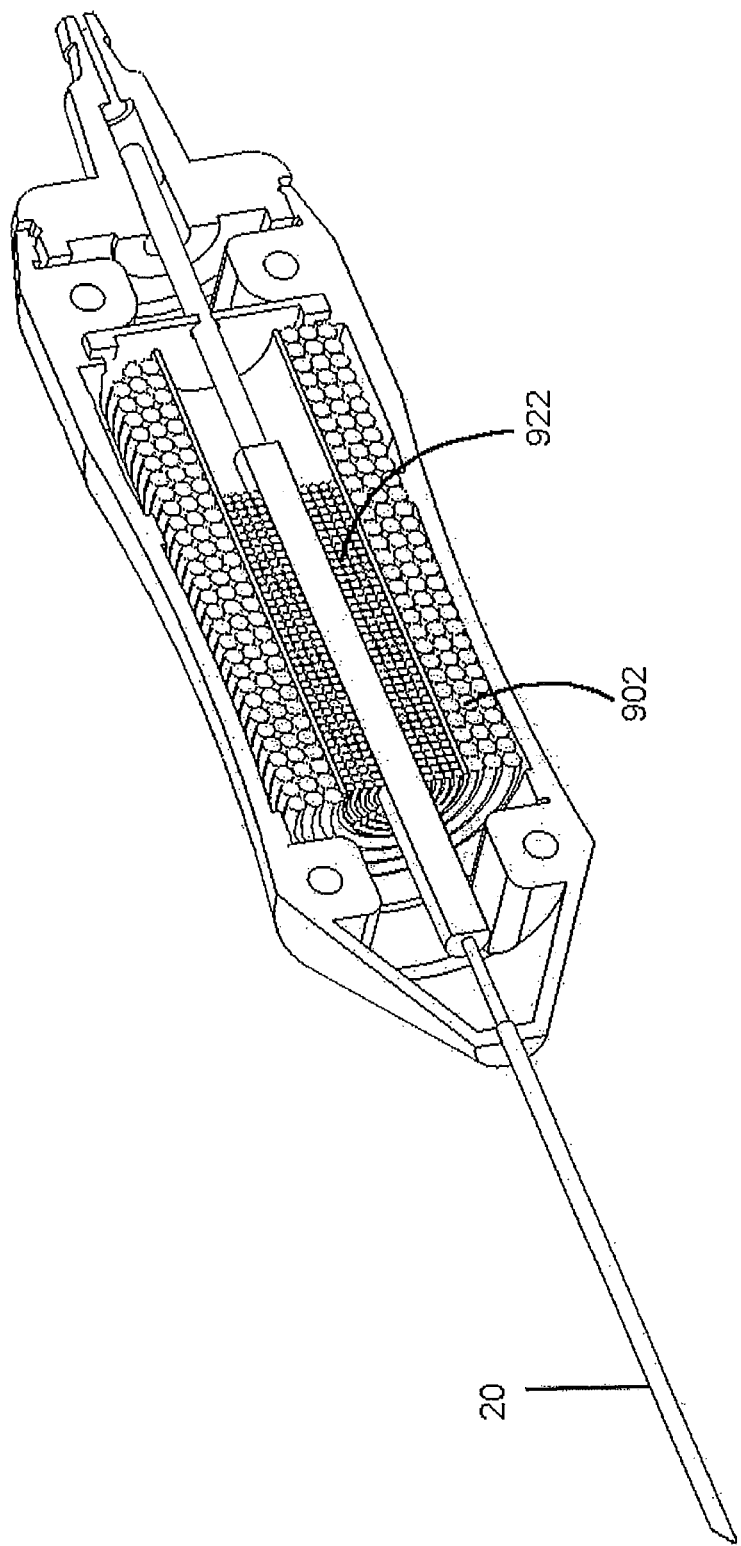
FIG. 20c is an isometric cross-sectional view of the tenth embodiment of the present invention using two coils.

FIG. 20*c* depicts another embodiment of the present invention using a voice coil type actuating mechanism and is of a different configuration than that used in FIGS. 20*a* and 20*b*. For example, in this alternative embodiment, a voice-coil actuating mechanism is substituted with a dual-coil actuating mechanism and as a result of this substitution, the magnetic member 904 of the voice-coil is replaced with second conductive coil 922. In other words, the second conductive coil 922 is wrapped around and attached to the driving tube 912 and the first conductive coil 902 is located, as in the first preferred embodiment, along an outside radius of the coil support tube 906. In a first embodiment of the configuration of FIG. 20*c*, the inner coil 922 is conducting direct current DC and the outer coil is conducting alternating current AC. In an alternative embodiment, the inner coil is conducting alternating current AC and the outer coil is conducting direct current DC. In an additional embodiment, both the inner coil and the outer coil are conducting alternating current AC.

Figure 20D:
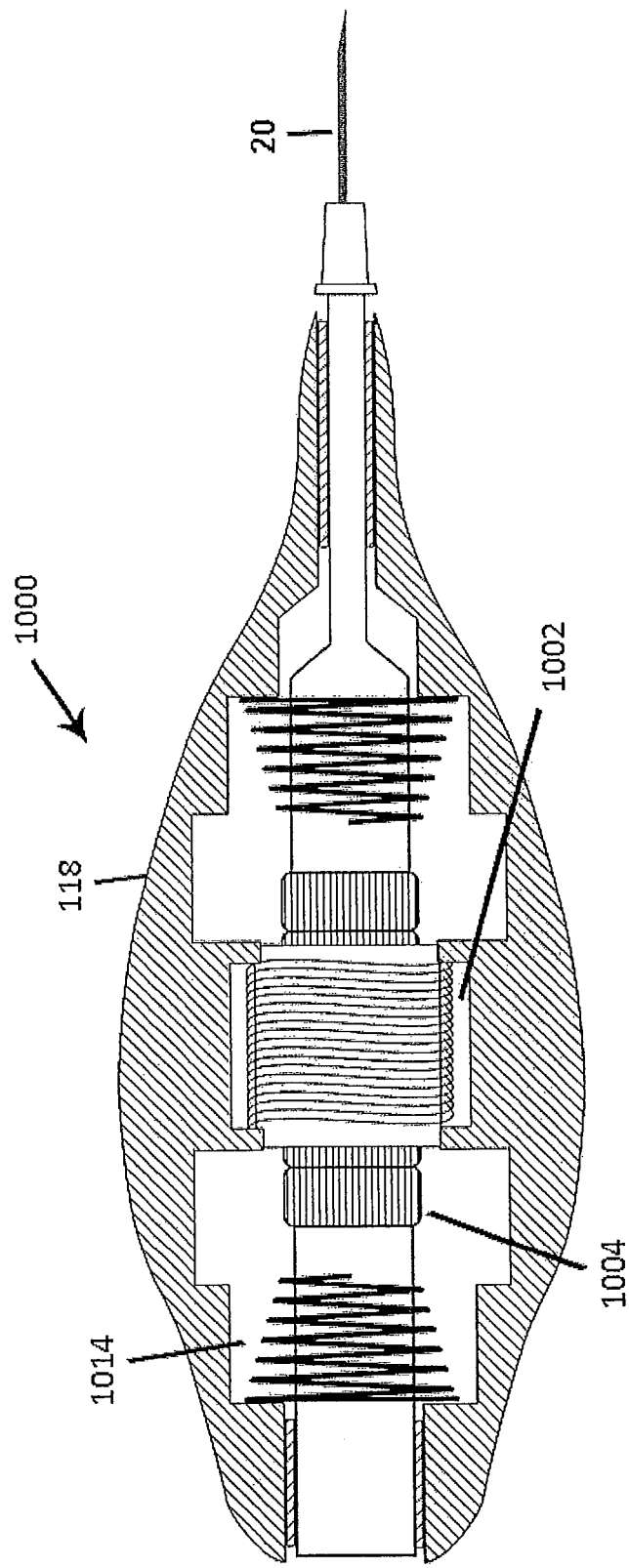
FIG. 20d is a side cross-sectional view of the tenth embodiment of the present invention using a solenoid with springs.

In all of the voice coil actuator configurations described, springs may be used to limit and control certain dynamic aspects of the penetrating member 20. FIG. 20*d* depicts another variation of the voice coil actuator mechanism of the tenth embodiment using springs, Medical Tool using solenoid actuator 1000. As with the other voice coil embodiments using coils, the basic principle of actuation is caused by a time varying magnetic field created inside a solenoid coil 1002 which acts on a set of very strong permanent magnets. The magnets 1004 and the entire penetrating member 20 assembly oscillate back and forth through the solenoid coil 1002. The springs 1014 (such as those shown in FIG. 20*d*) absorb and release energy at each cycle, amplifying the vibration seen at the penetrating member 20. The resonant properties of the device can be optimized by magnet selection, number of coil turns in the solenoid, mass of the shaft, and the stiffness of the springs.

Figure 21:
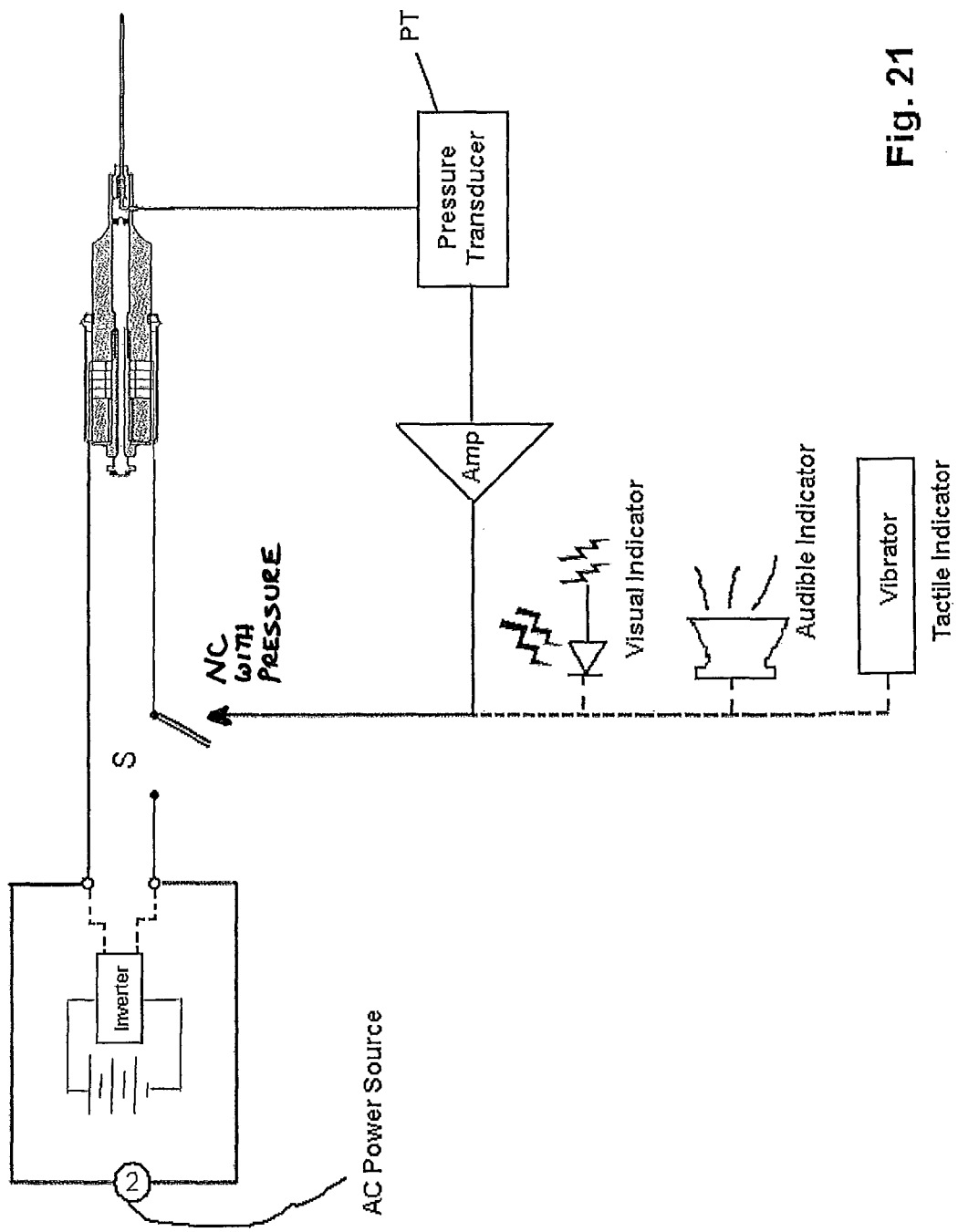
FIG. 21 is an exemplary schematic of an electrical power cut off for use in the various embodiments of the present invention.

From the above description, it may be appreciated that the present invention provides significant benefits over conventional medical devices. The configuration of the actuating means described above, such as embodiments comprising a Langevin actuator, Cymbal actuator, or an APA, accommodates the use of piezoelectric actuating members in a medical instrument by enabling the displacement of the penetrating sharps member or needle to such frequencies that cause a reduction of force needed for penetrating through tissue during procedures such as bone biopsy, epidural catheterization or vascular entry. Electrical signal control facilitated by an electrically coupled feedback system could provide the capability of high oscillation rate actuation, control over penetration depth, electrical cut off (faster response than human) and low traction force for these procedures. FIG. 21 depicts, by way of example only, an electrical cut off configuration. A pressure transducer PT monitors the pressure from the penetrating member 20 or of a fluid in communication with the tissue through the present invention. While the penetrating member 20 is penetrating tissue, the pressure detected by the pressure transducer PT is high and the switch S is normally closed. As soon as there is a drop in pressure (indicating passage through the final layer of tissue), the pressure transducer PT signal opens the switch S, thereby cutting off power to the medical tool. In addition, or a visual, audible or tactile indicator immediately activates warning the operator of sufficient passage by the penetrating member 20 and power cut off. It is within the broadest scope of the present invention to encompass a variety of power cut off configurations, including solid state switching and/or digital controls.

Another electrical power cut off implementation detects a forward motion of the biasing element 11 discussed previously. In particular, once the penetrating member 20 passes through the last tissue layer, pressure on the biasing element 11 is relieved and the incremental movement of the biasing element 11 into the body 10 is detected by a sensor which instantly opens the switch S and thereby cuts off electrical power to the present invention.

Additionally, the feedback control of the electronics enables the device to be vibrated in such a way that the force is also reduced as the penetrating member is retracted from the living being as would be necessary in bone biopsy after the tissue is extracted.

Now that exemplary embodiments of the present invention have been shown and described in detail, various modifications and improvements thereon will become readily apparent to those skilled in the art. While the foregoing embodiments may have dealt with the penetration through skin, bone, veins and ligaments as exemplary biological tissues, the present invention can undoubtedly ensure similar effects with other tissues which are commonly penetrated within the body. For example there are multiplicities of other tools like central venous catheter introducers, laparoscopic instruments with associated sharps, cavity drainage catheter kits, and neonatal lancets, as well as procedures like insulin administration and percutaneous glucose testing, to name a few, where embodiments disclosed herein comprising sonically or ultrasonically driven sharps members may be used to precisely pierce or puncture tissues with minimal tinting. Accordingly, the spirit and scope of the present invention is to be construed broadly and limited only by the appended claims, and not by the foregoing specification.

REFERENCE LABELS

A Static needle force curve
B Vibrating needle force curve
G1 Displacement Graph
LT Langevin actuator (also known as Langevin transducer)
PA1 Conventional biopsy needle
PA2 Conventional epidural needle
PA3 Conventional Syringe
PT Pressure transducer
S Switch
SP Side Port
ZN Zero node
1 Cannula
1' Cannula distal end
2 Stylet
3 Distal tip
4 Stylet tip angled face
5 Tuohy needle
6 Tuohy curved tip
7 Tip opening
9 Front portion
10 Tubular body
11 Biasing element
12 Plunger
14 Inner Stylet
15 Outer trocar tube
16 APA needle
16*b* Alternate embodiment
20 Penetrating member
100 Langevin actuator
110 Horn
111 Support wings
112 Rear mass
114 Piezoelectric elements
114*b* Electrical conductors
115 Sterilization sleeve
116 Bolt
117 Battery & inverter compartment
118 Handle
120 Seal
121 Distal face
122 Distal opening
123 Luer taper nose
124 Proximal opening
126 Bore
126*a* Short bore
128 Attachment fitting
129 Catheter
130 Hollow needle
130*a* Distal end of hollow needle
130*b* Proximal end of hollow needle
132 Plunger handle
134 Plunger shaft
134*a* Proximal end of plunger shaft
134*b* Distal end of plunger shaft
136 Plunger seal
142 Inner stylet handle 144 Inner stylet shaft
146 Inner stylet tip
148 Trocar attachment fitting
150 Outer trocar body
152 Distal trocar opening
154 Distal trocar tip
200 Penetrating introducer
202*b* More preferred embodiment
202*c* Most preferred embodiment
201 Supported introducer
202 Catheterization introducer
300 Bone biopsy device
400 Advanced bone biopsy device
500 APA syringe
500*b* Alternate embodiment
510 Amplified piezoelectric actuator (APA)
512 Frame
512*a* Proximal end of frame
512*b* Distal end of frame
513 Penetrating member
513*a* Proximal end of penetrating member
513*b* Distal tip of penetrating member
514 Piezoelectric material
516 APA attachment point
518 Handle
521 Handle distal opening
524 Handle proximal opening
525 Penetrating member hub
526 APA bore
600 Cymbal syringe
600*b* Alternate embodiment
610 Cymbal actuator
612 Endcap
612*a* Proximal endcap
612*b* Distal endcap
626 Cymbal bore
616 Cymbal attachment point
700 General side port configuration
700*a* First side port configuration
700*b* Second side port configuration
800 Feedback capable reduction of force tool
900 Medical tool using voice coil actuator
900*b* Alternate voice coil embodiment
902 Conducting coil
904 Magnetic member
906 Coil support tube
910 Body
912 Driving tube
914 Extension member
916*a* First attachment point
916*b* Second attachment point
918 First conductive attachment site
920 Second conductive attachment site
922 Second conductive coil
1000 Medical tool using solenoid actuator
1002 Solenoid coil
1004 Magnets
1014 Spring
1020 Pressure feedback system
1021 Reservoir with integrated pump
1022 Flexible tubing
1023 Attachment fitting
1024 Base
1025 On/off switch
1026 Light emitting diode

What is claimed is:

1. A medical device for penetrating living being tissue, said device comprising:
a penetrating member which is vibrated to reduce force needed to penetrate living being tissue;
a driving actuator coupled to said penetrating member and causing said vibration when energized; and
an electrical power cut off automatically de-energizing said medical device when said penetrating member has passed through said living being tissue,
wherein said driving actuator comprises:
a distal end coupled to said penetrating member;
a first channel extending to said distal end;
at least one piezoelectric element for converting electrical energy into oscillatory motion when energized, wherein a third channel extends through said at least one piezoelectric element such that said at least one piezoelectric element is disposed circumferentially completely around a length of said third channel; and
a second channel having a first end in communication with said first channel and a second end positioned at an exterior surface of said actuator, and
wherein said distal end and said penetrating member are displaced in oscillatory motion when said at least one piezoelectric element is energized.

2. The medical device of claim 1 wherein said at least one piezoelectric element is adapted for vibrating at a frequency to produce sinusoidal displacement of said penetrating member.

3. The medical device of claim 1
wherein said first channel and said third channel are in fluidic communication.

4. The medical device of claim 1 wherein said penetrating member further comprises a channel, and said first channel is in communication with said channel of said penetrating member.

5. The medical device of claim 1 wherein said driving actuator is a Langevin actuator.

6. The medical device of claim 5 wherein said distal end of said Langevin actuator defines an anti-node.

7. The medical device of claim 1 wherein said second channel extends radially from a longitudinal axis of said actuator and is centered at a location defining a zero-node.

8. The medical device of claim 1, wherein said driving actuator further comprises an anchor having a fourth channel, wherein the fourth channel extends longitudinally through the anchor, said fourth channel being in fluidic communication with said first and third channels.

9. The medical device of claim 1 wherein said second end of said second channel defines a side port for providing fluid communication with, or passage of a catheter within, said penetrating member.

10. The medical device of claim 1 further comprising a bolt disposed in said third channel, wherein said third channel has a circular cross-section.

11. The medical device of claim 10 wherein said bolt is hollow.

12. A medical device for penetrating living being tissue, said device comprising:
a penetrating member which is vibrated to reduce force needed to penetrate living being tissue,
a driving actuator coupled to said penetrating member and causing said vibration when energized, wherein said driving actuator has at least one piezoelectric element wherein a channel extends through said at least one piezoelectric element such that said at least one piezoelectric element is disposed circumferentially completely around a length of said channel; and an electrical power cut off automatically de-energizing said medical device when said penetrating member has passed through said living being tissue, wherein an exterior surface of said driving actuator comprises a side port for providing fluid communication with, or passage of a catheter within, said penetrating member.

13. A medical device for penetrating living being tissue, said device comprising:

a penetrating member which is vibrated to reduce force needed to penetrate living being tissue, a driving actuator coupled to said penetrating member and causing said vibration when energized, wherein said driving actuator has at least one piezoelectric element wherein a piezoelectric element channel extends through said at least one piezoelectric element such that said at least one piezoelectric element is disposed circumferentially completely around a length of said piezoelectric element channel;

an electrical power cut off automatically de-energizing said medical device when said penetrating member has passed through said living being tissue; and a fluid-containing syringe coupled to said driving actuator, said fluid-containing syringe comprising a moveable biasing element disposed therein, wherein said biasing element is in fluid communication with a channel within said penetrating member, said biasing element providing an indicator when said penetrating member has passed through said living being tissue.

14. The medical device of claim 13, further comprising a needle attachment fitting coupled to said penetrating member and to the driving actuator, wherein said biasing element comprises a moveable plunger disposed in said fluid-containing syringe, and wherein said fluid-containing syringe is coupled to a port of said attachment fitting.

15. The medical device of claim 14 wherein said plunger is used to aspirate matter from said living being via said medical device.

16. The medical device of claim 13, wherein said biasing element provides one of a visual, audible, or tactile indication that said penetrating member has passed through the living being tissue.

17. The medical device of claim 13 wherein said biasing element activates said electrical power cut off.

18. The medical device of claim 13, wherein the driving actuator comprises a port in fluid communication with said channel of said penetrating member, and the fluid-containing syringe is coupled to said actuator via said port.

19. A medical device for penetrating living being tissue, said device comprising:

a penetrating member which is vibrated to reduce force needed to penetrate living being tissue, a driving actuator coupled to said penetrating member and causing said vibration when energized, wherein said driving actuator has at least one piezoelectric element wherein a channel extends completely through said at least one piezoelectric element such that said at least one piezoelectric element is disposed circumferentially completely around a length of said channel;

an electrical power cut off automatically de-energizing said medical device when said penetrating member has passed through said living being tissue; and a loss of resistance pump system interfaced with said driving actuator, said loss of resistance pump comprising a visual indicator that automatically indicates entry of said penetrating member within a desired bodily area.

20. The medical device of claim 19 wherein said visual indicator comprises an LED.

* * * * *